United States Patent
Teufel et al.

(10) Patent No.: US 10,994,019 B2
(45) Date of Patent: May 4, 2021

(54) BICYCLIC PEPTIDE-TOXIN CONJUGATES SPECIFIC FOR MT1-MMP

(71) Applicant: BicycleRD Limited, Cambridge (GB)

(72) Inventors: Daniel Teufel, Cambridge (GB); Silvia Pavan, Cambridge (GB); Leonardo Baldassarre, Cambridge (GB)

(73) Assignee: BicycleRD Limited, Cambridge (GB)

( * ) Notice: Subject to any disclaimer, the term of this patent is extended or adjusted under 35 U.S.C. 154(b) by 2 days.

(21) Appl. No.: 16/097,305

(22) PCT Filed: May 4, 2017

(86) PCT No.: PCT/GB2017/051250
§ 371 (c)(1),
(2) Date: Oct. 29, 2018

(87) PCT Pub. No.: WO2017/191460
PCT Pub. Date: Nov. 9, 2017

(65) Prior Publication Data
US 2019/0134213 A1 May 9, 2019

(30) Foreign Application Priority Data
May 4, 2016 (GB) ..................... 1607827

(51) Int. Cl.
| A61K 31/5365 | (2006.01) |
| A61K 47/64 | (2017.01) |
| C07D 265/04 | (2006.01) |
| C07D 265/12 | (2006.01) |
| C07K 7/08 | (2006.01) |
| C07K 14/00 | (2006.01) |
| A61P 35/00 | (2006.01) |

(52) U.S. Cl.
CPC ...... *A61K 47/6415* (2017.08); *A61K 31/5365* (2013.01); *A61K 47/64* (2017.08); *A61P 35/00* (2018.01); *C07D 265/04* (2013.01); *C07D 265/12* (2013.01); *C07K 7/08* (2013.01); *C07K 14/00* (2013.01)

(58) Field of Classification Search
CPC ............... A61K 31/4365; A61K 47/64; A61K 47/6415; C07D 265/04; C07D 265/12; C07K 7/08; C07K 14/00
See application file for complete search history.

(56) References Cited

U.S. PATENT DOCUMENTS

| 8,680,022 B2 | 3/2014 | Gregory et al. |
| 8,685,890 B2 | 4/2014 | Winter et al. |
| 8,778,844 B2 | 7/2014 | Winter et al. |
| 9,518,081 B2 | 12/2016 | Winter et al. |
| 9,644,201 B2 | 5/2017 | Winter et al. |
| 9,657,288 B2 | 5/2017 | Winter et al. |
| 9,670,482 B2 | 6/2017 | Winter et al. |
| 9,670,484 B2 | 6/2017 | Winter et al. |
| 9,932,367 B2 | 4/2018 | Stace et al. |
| 9,994,617 B2 | 6/2018 | Tite et al. |
| 10,118,947 B2 | 11/2018 | Teufel et al. |
| 10,294,274 B2 | 5/2019 | Teufel et al. |
| 10,441,663 B2 | 10/2019 | Bennett et al. |
| 10,532,106 B2 | 1/2020 | Teufel et al. |
| 10,792,368 B1 * | 10/2020 | Teufel ..................... C07K 7/08 |
| 2014/0256596 A1 | 9/2014 | Tite et al. |
| 2017/0067045 A1 | 3/2017 | Winter et al. |
| 2018/0200378 A1 | 7/2018 | Bennett et al. |
| 2018/0280525 A1 | 10/2018 | Teufel et al. |
| 2018/0311300 A1 | 11/2018 | Beswick et al. |
| 2018/0362585 A1 | 12/2018 | Teufel et al. |
| 2018/0371020 A1 | 12/2018 | Bennett et al. |
| 2019/0184025 A1 | 6/2019 | Chen et al. |
| 2019/0263866 A1 | 8/2019 | Chen et al. |
| 2019/0307836 A1 | 10/2019 | Keen et al. |
| 2019/0389907 A1 | 12/2019 | Teufel et al. |
| 2020/0129630 A1 | 4/2020 | Koehler et al. |
| 2020/0131228 A1 | 4/2020 | Beswick et al. |
| 2020/0171161 A1 | 6/2020 | Teufel et al. |

FOREIGN PATENT DOCUMENTS

| WO | 2004077062 | 9/2004 |
| WO | 2006078161 | 7/2006 |
| WO | 2009098450 | 8/2009 |
| WO | 2016067035 | 5/2016 |
| WO | WO-17191460 A1 | 11/2017 |
| WO | WO-18096365 A1 | 5/2018 |
| WO | 2018115203 | 6/2018 |
| WO | 2018115204 | 6/2018 |
| WO | 2018197509 | 11/2018 |
| WO | WO-18197893 A1 | 11/2018 |

(Continued)

OTHER PUBLICATIONS

Bouchard et al., "Antibody-drug conjugates-A new wave of cancer drugs," Bioorganic & Medicinal Chemistry Letters, vol. 24, Dec. 2014 (pp. 5357-5363).
Chang et al., "Subtiligase: A tool for semisynthesis of proteins," Proceedings of the National Academy of Science USA, vol. 91, No. 26, Jan. 1995 (pp. 12544-12548).
Cherney et al., "Macrocyclic Amino Carboxylates as Selective MMP-8 Inhibitors," Journal of Medicinal Chemistry, vol. 41, No. 11, May 1998 (pp. 1749-1751).
Dawson et al., "Synthesis of proteins by native chemical ligation," Science, vol. 266, No. 5186, Nov. 1994 (pp. 776-779).
Driggers et al., "The exploration of macrocycles for drug discovery—an underexploited structural class," Nature Reviews Drug Discovery, vol. 7, No. 7, Jul. 2008 (pp. 608-624).
Gentilucci et al., "Chemical modifications designed to improve peptide stability: incorporation of non-natural amino acids, pseudo-peptide bonds, and cyclization," Current Pharmaceutical Design, vol. 16, No. 28, Sep. 2010 (pp. 3185-3203).

(Continued)

*Primary Examiner* — Jeffrey E. Russel
(74) *Attorney, Agent, or Firm* — Andrea L.C. Reid; Paul R. Fleming; Dechert LLP

(57) ABSTRACT

The present invention relates to drug conjugates comprising bicyclic peptides specific for MT1-MMP conjugated to one or more effector and/or functional groups which have utility in targeted cancer therapy.

17 Claims, 4 Drawing Sheets

Specification includes a Sequence Listing.

(56) References Cited

FOREIGN PATENT DOCUMENTS

| WO | WO-20084305 A1 | 4/2020 |
|---|---|---|
| WO | WO-20089627 A1 | 5/2020 |

OTHER PUBLICATIONS

Gu et al., "The influence of the penetrating peptide iRGD on the effect of paclitaxel-loaded MT1-AF7p-conjugated nanoparticles on glioma cells," Biomaterials, vol. 34, Jul. 2013 (pp. 5138-5148).

Heinis et al., "Phage-encoded combinatorial chemical libraries based on bicyclic peptides," Nature Chemical Biology, vol. 5, No. 7, Jul. 2009 (pp. 502-507).

International Search Report and Written Opinion issued by the European Patent Office as Searching Authority for International Application No. PCT/GB2017/051250, dated Aug. 4, 2017 (10 pages).

Kellogg et al., "Disulfide-Linked Antibody-Maytansinoid Conjugates: Optimization of In Vivo Activity by Varying the Steric Hindrance at Carbon Atoms Adjacent to the Disulfide Linkage," Bioconjugate Chemistry, vol. 22, No. 4, Mar. 2011 (pp. 717-727).

Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog" The Journal of Organic Chemistry, vol. 50, No. 26, Dec. 1985 (pp. 5834-5838).

Nestor, "The medicinal chemistry of peptides," Current Medicinal Chemistry, vol. 16, No. 33, No Month Listed 2009 (pp. 4399-4418).

Schreiber and Fersht, "Rapid, electrostatically assisted association of proteins," Nature Structural and Molecular Biology, vol. 3, No. 5, May 1996 (pp. 427-431).

Sounni et al., "MT1-MMP expression promotes tumor growth and angiogenesis through an up-regulation of vascular endothelial growth factor expression," The FASEB Journal, vol. 16, No. 6, Apr. 2002 (pp. 555-564).

Timmerman et al., "Rapid and quantitative cyclization of multiple peptide loops onto synthetic scaffolds for structural mimicry of protein surfaces," ChemBioChem, vol. 6, No. 5, May 2005 (pp. 821-824).

Tugyi et al., "Partial D-amino acid substitution: Improved enzymatic stability and preserved Ab recognition of a MUC2 epitope peptide," Proceedings of the National Academy of Science USA, vol. 102, No. 2, Jan. 2005 (pp. 413-418).

Wang, "An exact mathematical expression for describing competitive binding of two different ligands to a protein molecule," FEBS Letters, vol. 360, No. 2, Feb. 1995 (pp. 111-114).

Wu et al., "Structures of the CXCR4 chemokine GPCR with small-molecule and cyclic peptide antagonists," Science, vol. 330, No. 6007, Nov. 2010 (pp. 1066-1071).

Xiong et al., "Crystal Structure of the Extracellular Segment of Integrin $\alpha V\beta 3$ in Complex with an Arg-Gly-Asp Ligand," Science, vol. 296, No. 5565, Apr. 2002 (pp. 151-155).

Yoshihara et al., "Tags for labeling protein N-termini with subtiligase for proteomics," Bioorganic & Medicinal Chemistry Letters, vol. 18, No. 22, Nov. 2008 (pp. 6000-6003).

Zhao et al., "Structural basis of specificity of a peptidyl urokinase inhibitor, upain-1," Journal of Structural Biology, vol. 160, No. 1, Oct. 2007 (pp. 1-10).

Zhu et al., "High-affinity peptide against MT1-MMP for in vivo tumor imaging, Journal of Controlled Release," vol. 150, No. 3, Mar. 2011 (pp. 248-255).

U.S. Appl. No. 16/838,367, filed Apr. 2, 2020.

U.S. Appl. No. 16/871,305, filed May 11, 2020.

* cited by examiner ial

SEQUENCE LISTING

```
<160> NUMBER OF SEQ ID NOS: 15

<210> SEQ ID NO 1
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 1

Cys Xaa Xaa Xaa Xaa Gly Cys Glu Asp Phe Tyr Xaa Xaa Cys
1               5                   10

<210> SEQ ID NO 2
<211> LENGTH: 14
<212> TYPE: PRT
<213> ORGANISM: Artificial
<220> FEATURE:
<223> OTHER INFORMATION: Synthetic Peptide

<400> SEQUENCE: 2

Cys Tyr Asn Glu Phe Gly Cys Glu Asp Phe Tyr Asp Ile Cys
1               5                   10

<210> SEQ ID NO 3
<211> LENGTH: 15
<212> TYPE: PRT
<213> ORGANISM: Artificial
<220> FEATURE:
<223> OTHER INFORMATION: Synthetic Peptide

<400> SEQUENCE: 3

Ala Cys Tyr Asn Glu Phe Gly Cys Glu Asp Phe Tyr Asp Ile Cys
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic Peptide

<400> SEQUENCE: 4

Cys Asp Ala Asn Glu Phe Gly Cys Glu Asp Phe Tyr Asp Ile Cys
```

```
1               5                   10                  15
```

```
<210> SEQ ID NO 5
<211> LENGTH: 17
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 5

Ala Xaa Ala Cys Ala Asn Glu Xaa Ala Cys Glu Asp Phe Tyr Asp Xaa
1               5                   10                  15

Cys

<210> SEQ ID NO 6
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 6

Cys Xaa Xaa Xaa Xaa Gly Cys Glu Asp Phe Tyr Xaa Xaa Cys
1               5                   10

<210> SEQ ID NO 7
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any naturally occurring amino acid

<400> SEQUENCE: 7

Cys Xaa Xaa Xaa Phe Gly Cys Glu Asp Phe Tyr Asp Ile Cys
1               5                   10

<210> SEQ ID NO 8
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (2)..(4)
<223> OTHER INFORMATION: Xaa can be any naturally occurring amino acid
```

```
<400> SEQUENCE: 8

Cys Xaa Xaa Xaa Phe Gly Cys Glu Asp Phe Tyr Asp Ile Cys
1               5                   10

<210> SEQ ID NO 9
<211> LENGTH: 14
<212> TYPE: PRT
<213> ORGANISM: Artificial
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 9

Cys Xaa Asn Xaa Phe Gly Cys Glu Asp Phe Tyr Asp Ile Cys
1               5                   10

<210> SEQ ID NO 10
<211> LENGTH: 14
<212> TYPE: PRT
<213> ORGANISM: Artificial
<220> FEATURE:
<223> OTHER INFORMATION: Synthetic Peptide

<400> SEQUENCE: 10

Cys Met Asn Gln Phe Gly Cys Glu Asp Phe Tyr Asp Ile Cys
1               5                   10

<210> SEQ ID NO 11
<211> LENGTH: 14
<212> TYPE: PRT
<213> ORGANISM: Artificial
<220> FEATURE:
<223> OTHER INFORMATION: Synthetic Peptide

<400> SEQUENCE: 11

Cys Phe Gly Glu Phe Gly Cys Glu Asp Phe Tyr Asp Ile Cys
1               5                   10

<210> SEQ ID NO 12
<211> LENGTH: 14
<212> TYPE: PRT
<213> ORGANISM: Artificial
<220> FEATURE:
<223> OTHER INFORMATION: Synthetic Peptide

<400> SEQUENCE: 12

Cys Val Asn Glu Phe Gly Cys Glu Asp Phe Tyr Asp Ile Cys
1               5                   10

<210> SEQ ID NO 13
<211> LENGTH: 14
<212> TYPE: PRT
<213> ORGANISM: Artificial
<220> FEATURE:
<223> OTHER INFORMATION: Synthetic Peptide

<400> SEQUENCE: 13

Cys Phe Asn Glu Phe Gly Cys Glu Asp Phe Tyr Asp Ile Cys
1               5                   10
```

```
<210> SEQ ID NO 14
<211> LENGTH: 14
<212> TYPE: PRT
<213> ORGANISM: Artificial
<220> FEATURE:
<223> OTHER INFORMATION: Synthetic Peptide

<400> SEQUENCE: 14

Cys Tyr Asn Glu Tyr Gly Cys Glu Asp Phe Tyr Asp Ile Cys
1               5                   10

<210> SEQ ID NO 15
<211> LENGTH: 14
<212> TYPE: PRT
<213> ORGANISM: Artificial
<220> FEATURE:
<223> OTHER INFORMATION: Synthetic Peptide

<400> SEQUENCE: 15

Cys Tyr Asn Glu Trp Gly Cys Glu Asp Phe Tyr Asp Ile Cys
1               5                   10
```

BICYCLIC PEPTIDE-TOXIN CONJUGATES SPECIFIC FOR MT1-MMP

FIELD OF THE INVENTION

The present invention relates to drug conjugates comprising bicyclic peptides specific for MT1-MMP conjugated to one or more effector and/or functional groups which have utility in targeted cancer therapy.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å$^2$; Wu et al. (2007), Science 330, 1066-71), a cyclic peptide with the Arg-Gly-Asp motif binding to integrin αVb3 (355 Å$^2$) (Xiong et al. (2002), Science 296 (5565), 151-5) or the cyclic peptide inhibitor upain-1 binding to urokinase-type plasminogen activator (603 Å$^2$; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclisation of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO2009/098450). Briefly, combinatorial libraries of linear peptides containing three cysteine residues and two regions of six random amino acids (Cys-(Xaa)$_6$-Cys-(Xaa)$_6$-Cys) were displayed on phage and cyclised by covalently linking the cysteine side chains to a small molecule (tris-(bromomethyl)benzene).

SUMMARY OF THE INVENTION

According to a first aspect of the invention, there is provided a drug conjugate of formula (I):

(I)

[Structural formula showing Toxin connected via linker with R$_1$, R$_2$, R$_3$, R$_4$ groups, disulfide bridge, and subscripts n and m, to Bicycle]

wherein R$_1$ and R$_2$ both represent hydrogen;
R$_3$ and R$_4$ both represent C$_{1-6}$ alkyl;
n represents an integer selected from 1 to 10;
m represents an integer selected from 0 to 10;
Toxin refers to a cytotoxic agent;
Bicycle represents a peptide ligand specific for MT1-MMP comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises an amino acid sequence of formula (II):

(II)
(SEQ ID NO: 1)
-C$_i$-X$_1$-U/O$_2$-X$_3$-X$_4$-G$_5$-C$_{ii}$-E$_6$-D$_7$-F$_8$-Y$_9$-X$_{10}$-X$_{11}$-C$_{iii}$- or a pharmaceutically acceptable salt thereof;
wherein:
C$_i$, C$_{ii}$ and C$_{iii}$ represent first, second and third cysteine residues, respectively;
X represents any amino acid residue;
U represents a polar, uncharged amino acid residue selected from N, C, Q, M, S and T; and
O represents a non-polar aliphatic amino acid residue selected from G, A, I, L, P and V.

According to a further aspect of the invention, there is provided a pharmaceutical composition comprising a drug conjugate as defined herein in combination with one or more pharmaceutically acceptable excipients.

According to a further aspect of the invention, there is provided a drug conjugate as defined herein for use in preventing, suppressing or treating cancer, in particular solid tumours such as non-small cell lung carcinomas.

DETAILED DESCRIPTION OF THE INVENTION

Figure 1:
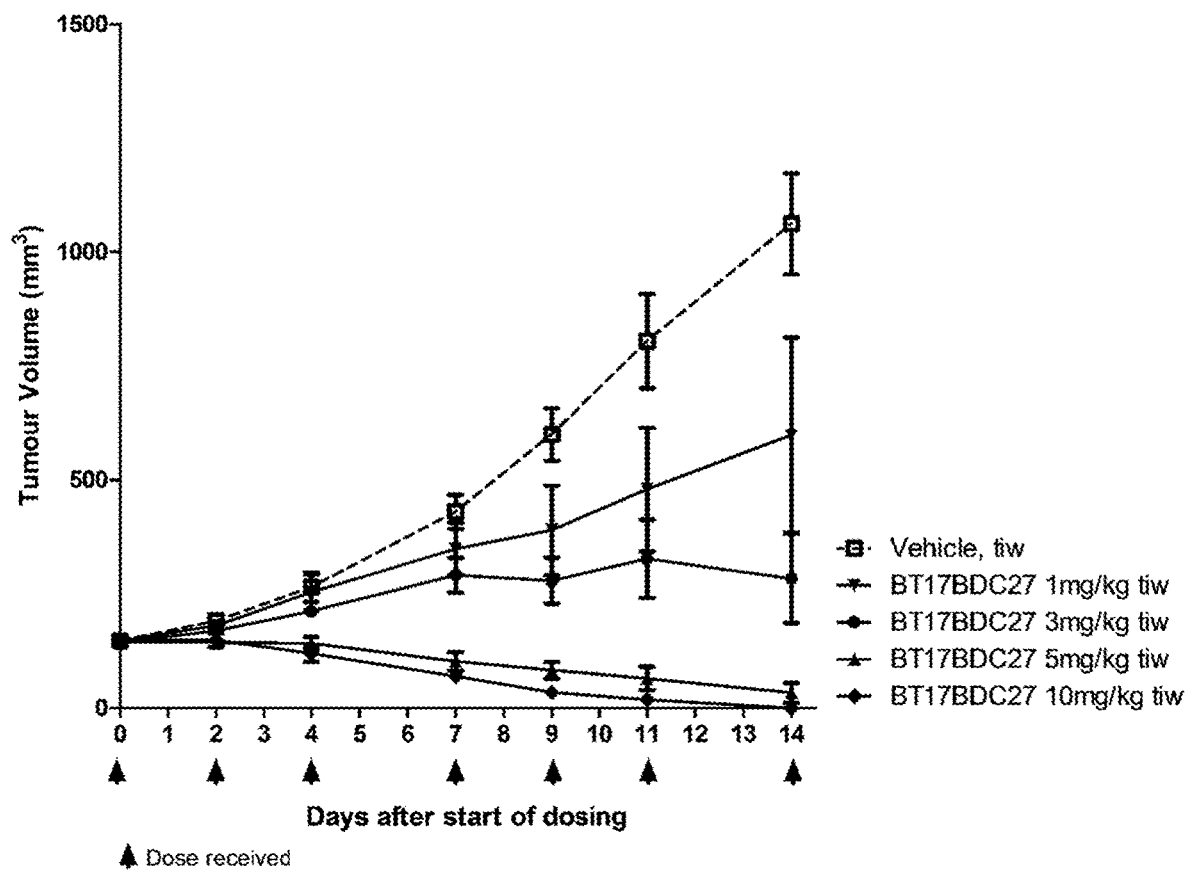
FIG. 1: Plot of mean tumour volume versus time for BT17BDC-27 in EBC-1 xenograft mice. Doses were administered on day 0, 2, 4, 7, 9, 11 and 14.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.), which are incorporated herein by reference.

Drug Conjugates

According to a first aspect of the invention, there is provided a drug conjugate of formula (I):

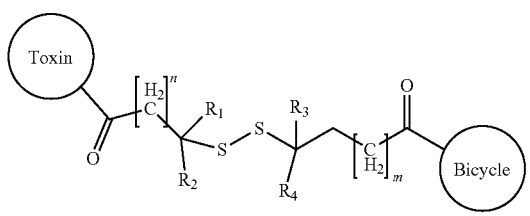

(I)

wherein $R_1$ and $R_2$ both represent hydrogen;
$R_3$ and $R_4$ both represent $C_{1-6}$ alkyl;
n represents an integer selected from 1 to 10;
m represents an integer selected from 0 to 10;
Toxin refers to a cytotoxic agent;
Bicycle represents a peptide ligand specific for MT1-MMP comprising a polypeptide comprising at least three cysteine residues, separated by at least two loop sequences, and a molecular scaffold which forms covalent bonds with the cysteine residues of the polypeptide such that at least two polypeptide loops are formed on the molecular scaffold, wherein the peptide ligand comprises an amino acid sequence of formula (II):

(II)
(SEQ ID NO: 1)
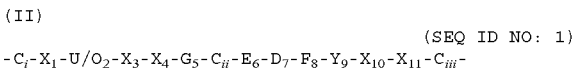

or a pharmaceutically acceptable salt thereof;
wherein:
$C_i$, $C_{ii}$ and $C_{iii}$ represent first, second and third cysteine residues, respectively;
X represents any amino acid residue;
U represents a polar, uncharged amino acid residue selected from N, C, Q, M, S and T; and
O represents a non-polar aliphatic amino acid residue selected from G, A, I, L, P and V.

In one particular embodiment of the invention, the cytotoxic agent is selected from: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin, calicheamycins, and others.

In one further particular embodiment of the invention, the cytotoxic agent is selected from maytansinoids (such as DM1) or monomethyl auristatins (such as MMAE).

DM1 is a cytotoxic agent which is a thiol-containing derivative of maytansine and has the following structure:

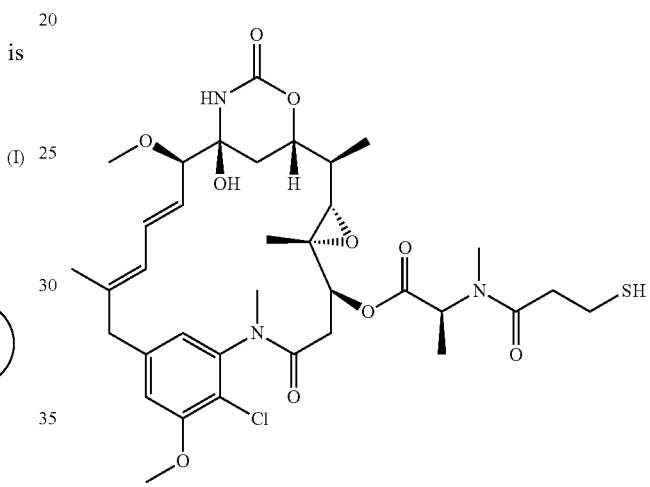

Monomethyl auristatin E (MMAE) is a synthetic antineoplastic agent and has the following structure:

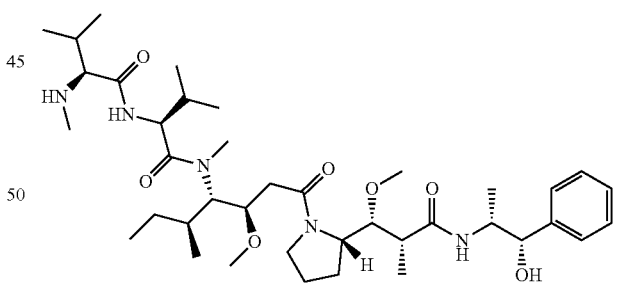

Data is presented herein in Examples 1 to 3 which demonstrates the effects of peptide ligands conjugated to toxins containing DM1.

The term $C_{1-6}$ alkyl as used herein refers to a linear or branched saturated hydrocarbon group containing from 1 to 6 carbon atoms, respectively. Examples of such groups include methyl, ethyl, n-propyl, isopropyl, n-butyl, isobutyl, sec-butyl, tert butyl, n-pentyl, isopentyl, neopentyl or hexyl and the like.

In one embodiment, $R^3$ and $R^4$ are both methyl.
In one embodiment, n represents 1.
In one embodiment, m represents 1.

In one embodiment, R³ and R⁴ are both methyl, n represents 1 and m represents 1.

In one embodiment, the toxin is a maytansine and the conjugate comprises a compound of formula (III):

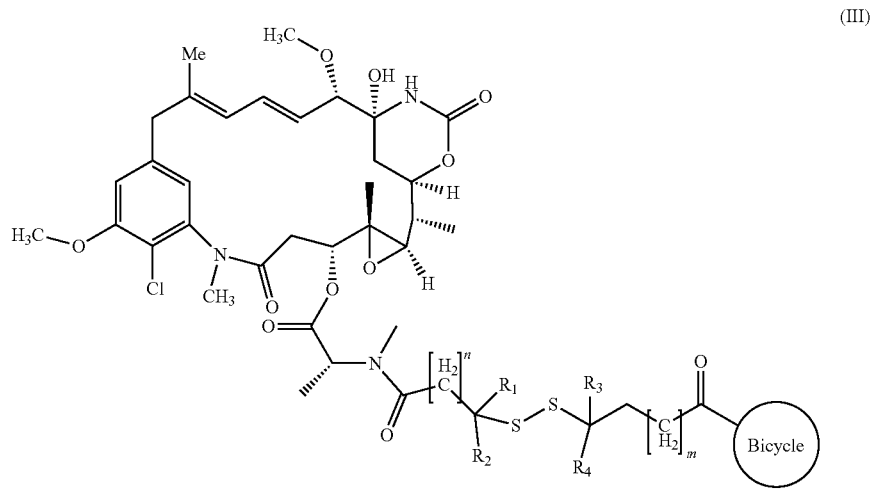

(III)

wherein $R_1$, $R_2$, $R_3$, $R_4$, n, m and Bicycle are as defined herein.

In a further embodiment of the conjugate of formula (III), n and m both represent 1, $R_1$ and $R_2$ both represent hydrogen and $R_3$ and $R_4$ both represent methyl, i.e. a compound of formula (III)$^a$:

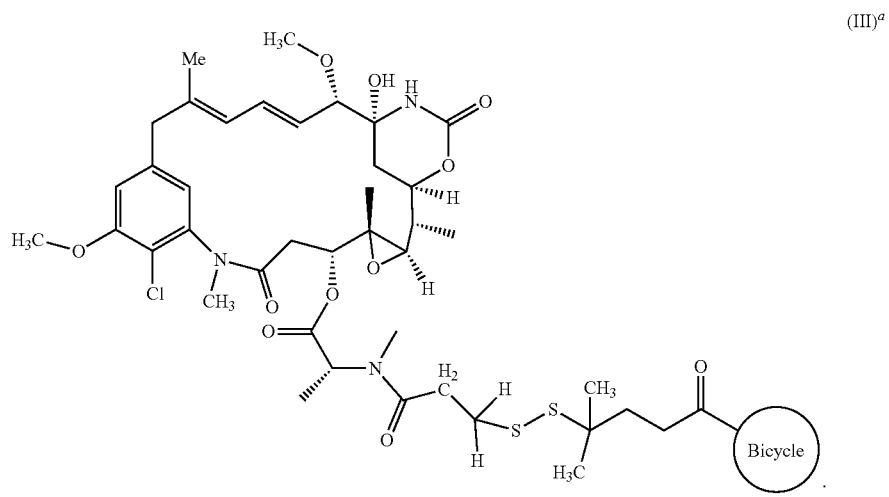

(III)$^a$

In a yet further embodiment, the conjugate of formula (III) or (III)$^a$ is selected from BT17BDC-27:

[Chemical structure of maytansine-disulfide conjugate with Bicycle 17-69-07-N268]

or BT17BDC-28:

[Chemical structure of maytansine-disulfide conjugate with Bicycle 17-69-07-N241]

BT17BDC-28 employs the stabilised Bicyclic peptide counterpart (17-69-07-N241) which is amide-bonded to the toxin-disulphide construct. This non-hindered derivative of the maytansine with n=1 is termed DM1. The molecule contains two hindering methyl groups on the Bicycle side, and in the antibody drug conjugate context produces a 14-fold reduction in its sensitivity to a reducing agent such as dithiothreitol. The reduced sensitivity to reduction is correlated with a lower toxin release rate.

BT17BDC-27 employs the stabilised Bicyclic peptide counterpart (17-69-07-N268) lacking the bAla-Sar10 molecular spacer of 17-69-07-N241, and which is amide-bonded to the toxin-disulphide construct. The absence of the molecular spacer provides a smaller overall molecule, at reduced synthetic costs, with a higher toxin to API ratio. This non-hindered derivative of the maytansine with n=1 is termed DM1. The molecule contains two hindering methyl groups on the Bicycle side, and in the antibody drug conjugate context produces a 14-fold reduction in its sensitivity to a reducing agent such as dithiothreitol. The reduced sensitivity to reduction is correlated with a lower toxin release rate.

Nomenclature
Numbering

When referring to amino acid residue positions within compounds of formula (II), cysteine residues ($C_i$, $C_{ii}$ and $C_{iii}$) are omitted from the numbering as they are invariant, therefore, the numbering of amino acid residues within the compound of formula (II) is referred to as below:

(SEQ ID NO: 1)
-$C_i$-$X_1$-U/$O_2$-$X_3$-$X_4$-$G_5$-$C_{ii}$-$E_6$-$D_7$-$F_8$-$Y_9$-$X_{10}$-$X_{11}$-$C_{iii}$-.

For the purpose of this description, all bicyclic peptides are assumed to be cyclised with TBMB (1,3,5-tris(bromomethyl)benzene) yielding a tri-substituted 1,3,5-trismethylbenzene structure. Cyclisation with TBMB occurs on $C_i$, $C_{ii}$, and $C_{iii}$.

Bicyclic Peptide Core Sequence

Each bicyclic peptide disclosed herein has been assigned a unique core sequence number which is defined as the amino acid sequence between the first N-terminal Cysteine ($C_i$) and the last C-terminal Cysteine ($C_{iii}$). In the example of the identifier 17-69-07, the core sequence is $C_i$YNEFGC$_{ii}$-EDFYDIC$_{iii}$ (SEQ ID NO: 2), and is referred to as "17-69-07" or "(17-69-07)".

Peptide Code

Certain bicyclic peptides disclosed herein have also been assigned a unique identifier using a peptide code, such as 17-69-07-N241, wherein N241 denotes a particular derivative of the 17-69-07 bicycle core sequence. Different derivatives of 17-69-07 have different N-numbers, i.e. N001, N002, Nxxx.

Molecular Format

N- or C-terminal extensions to the bicycle core sequence are added to the left or right side of the core sequence, separated by a hyphen. For example, an N-terminal bAla-Sar10-Ala tail would be denoted as:

```
bAla-Sar10-A-(17-69-07)
                                    (SEQ ID NO: 3)
and has the full sequence of βAla-Sar10-A-CYNEFGCEDFYDIC.
```

Modifications

Non-natural amino acid substitutions within the bicycle core sequence are indicated after the Molecular Format description. For example, if Tyrosine 1 in 17-69-07 is substituted with D-Alanine, the description is (17-69-07) D-Ala1, and the full sequence would be described as C(D-Ala1)NEFGCEDFYDIC (SEQ ID NO: 4).

If an N-terminal or C-terminal tail is attached to a bicyclic peptide that also contains modifications to the core sequence, then, by using 17-69-07-N241 as an example, the Molecular Format description is:

bAla-Sar10-A-(17-69-07) DAla1 1Nal4 DAla5 tBu-Gly11.

The full amino acid sequence of 17-69-07-N241 is therefore:

```
                                    (SEQ ID NO: 5)
bAla-Sar10-A-C(D-Ala)NE(1Nal)(D-

Ala)CEDFYD(tBuGly)C.
```

Bicyclic Peptide Ligands of Formula (II)

A peptide ligand, as referred to herein, refers to a peptide covalently bound to a molecular scaffold. Typically, such peptides comprise two or more reactive groups (i.e. cysteine residues) which are capable of forming covalent bonds to the scaffold, and a sequence subtended between said reactive groups which is referred to as the loop sequence, since it forms a loop when the peptide is bound to the scaffold. In the present case, the peptides comprise at least three cysteine residues (referred to herein as $C_i$, $C_{ii}$ and $C_{iii}$), and form at least two loops on the scaffold.

It will be appreciated by the skilled person that the X at positions 1, 3, 4, 10 and 11 of formula (II) may represent any amino acid following the results of an alanine scan and selection outputs which permits well tolerated substitutions at these positions.

In one embodiment, the X at position 1 of formula (II) is selected from any one of the following amino acids: Y, M, F or V. In a further embodiment, the X at position 1 of formula (II) is selected from Y, M or F. In a yet further embodiment, the X at position 1 of formula (II) is selected from Y or M. In a still yet further embodiment, the X at position 1 of formula (II) is selected from Y.

In one embodiment, the U/O at position 2 of formula (II) is selected from a U, such as an N. In an alternative embodiment, the U/O at position 2 of formula (II) is selected from an O, such as a G.

In one embodiment, the X at position 3 of formula (II) is selected from U or Z, wherein U represents a polar, uncharged amino acid residue selected from N, C, Q, M, S and T and Z represents a polar, negatively charged amino acid residue selected from D or E. In a further embodiment, the U at position 3 of formula (II) is selected from Q. In an alternative embodiment, the Z at position 3 of formula (II) is selected from E.

In one embodiment, the X at position 4 of formula (II) is selected from J, wherein J represents a non-polar aromatic amino acid residue selected from F, W and Y. In a further embodiment, the J at position 4 of formula (II) is selected from F. In alternative embodiment, the J at position 4 of formula (II) is selected from Y. In alternative embodiment, the J at position 4 of formula (II) is selected from W.

In one embodiment, the X at position 10 of formula (II) is selected from Z, wherein Z represents a polar, negatively charged amino acid residue selected from D or E. In one embodiment, the Z at position 10 of formula (II) is selected from D.

In one embodiment, the X at position 11 of formula (II) is selected from O, wherein O represents a non-polar aliphatic amino acid residue selected from G, A, I, L, P and V. In one embodiment, the O at position 11 of formula (II) is selected from I.

In one embodiment, the compound of formula (II) is a compound of formula (IIa):

(IIa)
                                          (SEQ ID NO: 6)
-$C_i$-Y/M/F/V-U/O-U/Z-J-G-$C_{ii}$-E-D-F-Y-Z-O-$C_{iii}$-;

wherein U, O, J and Z are as defined hereinbefore.

In one embodiment, the compound of formula (II) is a compound of formula (IIb):

(IIb)
                                          (SEQ ID NO: 7)
-$C_i$-Y/M/F/V-N/G-E/Q-F-G-$C_{ii}$-E-D-F-Y-D-I-$C_{iii}$-.

In one embodiment, the compound of formula (II) is a compound of formula (IIc):

(IIc)
                                          (SEQ ID NO: 8)
-$C_i$-Y/M/F-N/G-E/Q-F-G-$C_{ii}$-E-D-F-Y-D-I-$C_{iii}$-.

In one embodiment, the compound of formula (II) is a compound of formula (IId):

(IId)
                                          (SEQ ID NO: 9)
-$C_i$-Y/M-N-E/Q-F-G-$C_{ii}$-E-D-F-Y-D-I-$C_{iii}$-.

In one embodiment, the compound of formula (II) is a compound of formula (IIe):

(IIe)
                                          (SEQ ID NO: 2)
-$C_i$-Y-N-E-F-G-$C_{ii}$-E-D-F-Y-D-I-$C_{iii}$-(17-69-07).

In a yet further embodiment, the peptide of formula (II) comprises a sequence selected from:

-$C_i$-Y-N-E-F-G-$C_{ii}$-E-D-F-Y-D-I-$C_{iii}$-(17-69-07); (SEQ ID NO: 2)

-$C_i$-M-N-Q-F-G-$C_{ii}$-E-D-F-Y-D-I-$C_{iii}$-(17-69-12); (SEQ ID NO: 10)

-$C_i$-F-G-E-F-G-$C_{ii}$-E-D-F-Y-D-I-$C_{iii}$-(17-69-02); (SEQ ID NO: 11)

-$C_i$-V-N-E-F-G-$C_{ii}$-E-D-F-Y-D-I-$C_{iii}$-(17-69-03); (SEQ ID NO: 12)

-$C_i$-F-N-E-F-G-$C_{ii}$-E-D-F-Y-D-I-$C_{iii}$-(17-69-04); (SEQ ID NO: 13)

-$C_i$-Y-N-E-Y-G-$C_{ii}$-E-D-F-Y-D-I-$C_{iii}$-(17-69-07-N057); (SEQ ID NO: 14)
and -$C_i$-Y-N-E-W-G-$C_{ii}$-E-D-F-Y-D-I-$C_{iii}$-(17-69-44-N002). (SEQ ID NO: 15)

The peptides of this embodiment were identified to be potent candidates following affinity maturation against the hemopexin domain of MT1-MMP.

In a still yet further embodiment, the peptide of formula (II) comprises a sequence selected from:

-$C_i$-Y-N-E-F-G-$C_{ii}$-E-D-F-Y-D-I-$C_{iii}$-(17-69-07); (SEQ ID NO: 2)
and

-$C_i$-M-N-Q-F-G-$C_{ii}$-E-D-F-Y-D-I-$C_{iii}$-(17-69-12). (SEQ ID NO: 10)

The peptides of this embodiment were identified to be the highest affinity candidates following affinity maturation against the hemopexin domain of MT1-MMP, synthesis of the core bicycle sequences, and quantitative measurement of affinities using competition experiments.

In a still yet further embodiment, the peptide of formula (II) comprises a sequence selected from -$C_i$-Y-N-E-F-G-$C_{ii}$-E-D-F-Y-D-I-$C_{iii}$-(17-69-07) (SEQ ID NO: 2). The peptide of this embodiment was identified to be the most potent, and stable member of the family of peptide ligands within formula (II).

In a still yet further embodiment, the peptide of formula (II) comprises a sequence selected from:
bAla-Sar10-A-(17-69-07) D-Ala1 1Nal4 D-Ala5 tBu-Gly11 (17-69-07-N241, with the full sequence (bAla)-Sar10-A$C_i$(D-Ala)NE(1Nal)(D-Ala)$C_{ii}$EDFYD(tBu-Gly)$C_{iii}$); or
A-(17-69-07) D-Ala1 1Nal4 D-Ala5 tBuGly11 (17-69-07-N268, with the full sequence A$C_i$ (D-Ala)NE(1Nal)(D-Ala)$C_{ii}$EDFYD(tBuGly)$C_{iii}$), respectively, where the N-terminus is present as the free amino group, and the C-terminus is amidated.

Data is presented in Examples 1-3 which demonstrates favourable in vitro and in vivo properties of drug conjugates comprising these bicyclic peptides.

In one embodiment, certain peptides of formula (II) are fully cross-reactive with murine, dog, cynomolgus and human MT1-MMP. In a further embodiment, the specifically exemplified peptide ligands of the invention are fully cross-reactive with murine, dog, cynomolgus and human MT1-MMP. For example, both non-stabilised and stabilised derivatives of 17-69-07 (i.e. 17-69-07-N219, 17-69-07-N241 and 17-69-07-N268) are fully cross reactive.

In a yet further embodiment, the peptide of formula (II) is selective for MT1-MMP, but does not cross-react with MMP-1, MMP-2, MMP-15 and MMP-16. The 17-69-07 core sequence, and the stabilised variant 17-69-07-N258, are uniquely selective for MT1-MMP.

Advantages of the Peptide Ligands

Certain bicyclic peptides of formula (II) have a number of advantageous properties which enable them to be considered as suitable drug-like molecules for injection, inhalation, nasal, ocular, oral or topical administration. Such advantageous properties include:
Species cross-reactivity. This is a typical requirement for preclinical pharmacodynamics and pharmacokinetic evaluation;
Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;
Desirable solubility profile. This is a function of the proportion of charged and hydrophilic versus hydrophobic residues and intra/inter-molecular H-bonding, which is important for formulation and absorption purposes; and
An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent.

Pharmaceutically Acceptable Salts

It will be appreciated that salt forms are within the scope of this invention, and references to bicyclic peptide compounds of formula (II) include the salt forms of said compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g.

(+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydroiodic, phosphoric, nitric, sulfuric, citric, lactic, succinic, maleic, malic, isethionic, fumaric, benzenesulfonic, toluenesulfonic, sulfuric, methanesulfonic (mesylate), ethanesulfonic, naphthalenesulfonic, valeric, propanoic, butanoic, malonic, glucuronic and lactobionic acids. One particular salt is the hydrochloride salt. Another particular salt is the acetate salt.

If the compound is anionic, or has a functional group which may be anionic (e.g., —COOH may be —COO$^-$), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of formula (II) contain an amine function, these may form quaternary ammonium salts, for example by reaction with an alkylating agent according to methods well known to the skilled person. Such quaternary ammonium compounds are within the scope of formula (II).

Modified Derivatives

It will be appreciated that modified derivatives of the peptide ligands as defined herein are within the scope of the present invention. Examples of such suitable modified derivatives include one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more non-polar amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the alpha-carbon of one or more amino acid residues with another chemical group, modification of amino acids such as cysteine, lysine, glutamate/aspartate and tyrosine with suitable amine, thiol, carboxylic acid and phenol-reactive reagents so as to functionalise said amino acids, and introduction or replacement of amino acids that introduce orthogonal reactivities that are suitable for functionalisation, for example azide or alkyn-group bearing amino acids that allow functionalisation with alkyn or azide-bearing moieties, respectively.

In one embodiment, the modified derivative comprises a modification at amino acid position 1 and/or 9. These positions, especially where tyrosine is present, are most susceptible to proteolytic degradation.

In one embodiment, the modified derivative comprises an N-terminal and/or C-terminal modification. In a further embodiment, wherein the modified derivative comprises an N-terminal modification using suitable amino-reactive chemistry, and/or C-terminal modification using suitable carboxy-reactive chemistry. In a further embodiment, said N-terminal or C-terminal modification comprises addition of an effector group, including but not limited to a cytotoxic agent, a radiochelator or a chromophore.

In a further embodiment, the modified derivative comprises an N-terminal modification. In a further embodiment, the N-terminal modification comprises an N-terminal acetyl group. In this embodiment, the N-terminal cysteine group (the group referred to herein as C$_i$) is capped with acetic anhydride or other appropriate reagents during peptide synthesis leading to a molecule which is N-terminally acetylated. This embodiment provides the advantage of removing a potential recognition point for aminopeptidases and avoids the potential for degradation of the bicyclic peptide.

In an alternative embodiment, the N-terminal modification comprises the addition of a molecular spacer group which facilitates the conjugation of effector groups and retention of potency of the bicyclic peptide to its target, such as an Ala, G-Sar10-A or bAla-Sar10-A group. In one embodiment, the spacer group is selected from bAla-Sar10-A (i.e. 17-69-07-N241). Addition of these spacer groups to the bicyclic peptide 17-69-07 does not alter potency to the target protein.

In a further embodiment, the modified derivative comprises a C-terminal modification. In a further embodiment, the C-terminal modification comprises an amide group. In this embodiment, the C-terminal cysteine group (the group referred to herein as C$_{iii}$) is synthesized as an amide during peptide synthesis leading to a molecule which is C-terminally amidated. This embodiment provides the advantage of removing a potential recognition point for carboxypeptidase and reduces the potential for proteolytic degradation of the bicyclic peptide.

In one embodiment, the modified derivative comprises replacement of one or more amino acid residues with one or more non-natural amino acid residues. In this embodiment, non-natural amino acids may be selected having isosteric/isoelectronic side chains which are neither recognised by degradative proteases nor have any adverse effect upon target potency.

Alternatively, non-natural amino acids may be used having constrained amino acid side chains, such that proteolytic hydrolysis of the nearby peptide bond is conformationally and sterically impeded. In particular, these concern proline analogues, bulky sidechains, Cα-disubstituted derivatives (for example, aminoisobutyric acid, Aib), and cyclo amino acids, a simple derivative being amino-cyclopropylcarboxylic acid.

In one embodiment, the non-natural amino acid residue is substituted at position 4. A number of non-natural amino acid residues are well tolerated at this position. In a further embodiment, the non-natural amino acid residues, such as those present at position 4, are selected from: 1-naphthylalanine; 2-naphthylalanine; cyclohexylglycine, phenylglycine; tert-butylglycine; 3,4-dichlorophenylalanine; cyclohexylalanine; and homophenylalanine.

In a yet further embodiment, the non-natural amino acid residues, such as those present at position 4, are selected from: 1-naphthylalanine; 2-naphthylalanine; and 3,4-dichlorophenylalanine. These substitutions enhance the affinity compared to the unmodified wildtype sequence.

In a yet further embodiment, the non-natural amino acid residues, such as those present at position 4, are selected from: 1-naphthylalanine. This substitution provided the greatest level of enhancement of affinity (greater than 7 fold) compared to wildtype.

In one embodiment, the non-natural amino acid residue is introduced at position 9 and/or 11. A number of non-natural amino acid residues are well tolerated at these positions.

In a further embodiment, the non-natural amino acid residues, such as those present at position 9, are selected from: 4-bromophenylalanine, pentafluoro-phenylalanine, such as 4-bromophenylalanine.

In a yet further embodiment, the non-natural amino acid residues, such as those present at position 11, is selected from: tert-butylglycine. Enhancement of activity and strong protection of the vicinal amino acid backbone from proteolytic hydrolysis is achieved by steric obstruction.

In one embodiment, the modified derivative comprises a plurality of the above mentioned modifications, such as 2, 3, 4 or 5 or more modifications. In a further embodiment, the modified derivative comprises 2, 3, 4 or 5 or more of the following modifications, such as all of the following 5 modifications: D-alanine at position 1 and 5, a 1-naphthylalanine at position 4, a 4-bromophenylalanine at position 9 and a tert-butylglycine at position 11. This multi-substitution is tolerated in concert with potency which is superior to wildtype. In a yet further embodiment, the modified derivative comprises the following modifications: D-alanine at position 1 and 5, a 1-naphthylalanine at position 4 and a tert-butylglycine at position 11. This multi-substitution is tolerated in concert with potency which is superior to wildtype.

In one embodiment, the modified derivative comprises the addition of a spacer group. In a further embodiment, the modified derivative comprises the addition of a spacer group to the N-terminal cysteine ($C_i$) and/or the C-terminal cysteine ($C_{iii}$).

In one embodiment, the modified derivative comprises replacement of one or more oxidation sensitive amino acid residues with one or more oxidation resistant amino acid residues. In a further embodiment, the modified derivative comprises replacement of a tryptophan residue with a naphthylalanine or alanine residue. This embodiment provides the advantage of improving the pharmaceutical stability profile of the resultant bicyclic peptide ligand.

In one embodiment, the modified derivative comprises replacement of one or more charged amino acid residues with one or more hydrophobic amino acid residues. In an alternative embodiment, the modified derivative comprises replacement of one or more hydrophobic amino acid residues with one or more charged amino acid residues. The correct balance of charged versus hydrophobic amino acid residues is an important characteristic of the bicyclic peptide ligands. For example, hydrophobic amino acid residues influence the degree of plasma protein binding and thus the concentration of the free available fraction in plasma, while charged amino acid residues (in particular arginine) may influence the interaction of the peptide with the phospholipid membranes on cell surfaces. The two in combination may influence half-life, volume of distribution and exposure of the peptide drug, and can be tailored according to the clinical endpoint. In addition, the correct combination and number of charged versus hydrophobic amino acid residues may reduce irritation at the injection site (if the peptide drug has been administered subcutaneously).

In one embodiment, the modified derivative comprises replacement of one or more L-amino acid residues with one or more D-amino acid residues. This embodiment is believed to increase proteolytic stability by steric hindrance and by a propensity of D-amino acids to stabilise β-turn conformations (Tugyi et al (2005) PNAS, 102(2), 413-418).

In a further embodiment, the amino acid residue at position 1 is substituted for a D-amino acid, such as D-alanine. This substitution achieves retention of potency without the consequent degradation.

In a further embodiment, the amino acid residue at position 5 is substituted for a D-amino acid, such as D-alanine or D-arginine. This substitution achieves retention of potency without the consequent degradation.

In one embodiment, the modified derivative comprises removal of any amino acid residues and substitution with alanines. This embodiment provides the advantage of removing potential proteolytic attack site(s).

It should be noted that each of the above mentioned modifications serve to deliberately improve the potency or stability of the peptide. Further potency improvements based on modifications may be achieved through the following mechanisms:

Incorporating hydrophobic moieties that exploit the hydrophobic effect and lead to lower off rates, such that higher affinities are achieved;

Incorporating charged groups that exploit long-range ionic interactions, leading to faster on rates and to higher affinities (see for example Schreiber et al, *Rapid, electrostatically assisted association of proteins* (1996), Nature Struct. Biol. 3, 427-31); and Incorporating additional constraint into the peptide, by for example constraining side chains of amino acids correctly such that loss in entropy is minimal upon target binding, constraining the torsional angles of the backbone such that loss in entropy is minimal upon target binding and introducing additional cyclisations in the molecule for identical reasons.

(for reviews see Gentilucci et al, Curr. Pharmaceutical Design, (2010), 16, 3185-203, and Nestor et al, Curr. Medicinal Chem (2009), 16, 4399-418).

Isotopic Variations

The present invention includes all pharmaceutically acceptable (radio)isotope-labeled compounds of the invention, i.e. compounds of formula (II), wherein one or more atoms are replaced by atoms having the same atomic number, but an atomic mass or mass number different from the atomic mass or mass number usually found in nature, and compounds of formula (II), wherein metal chelating groups are attached (termed "effector") that are capable of holding relevant (radio)isotopes, and compounds of formula (I), wherein certain functional groups are covalently replaced with relevant (radio)isotopes or isotopically labelled functional groups.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, sulfur, such as $^{35}$S, copper, such as $^{64}$Cu, gallium, such as $^{67}$Ga or $^{68}$Ga, yttrium, such as $^{90}$Y and lutetium, such as $^{177}$Lu, and Bismuth, such as $^{213}$Bi.

Certain isotopically-labelled compounds of formula (II), for example, those incorporating a radioactive isotope, are useful in drug and/or substrate tissue distribution studies, and to clinically assess the presence and/or absence of the MT1-MMP target on diseased tissues such as tumours and elsewhere. The compounds of formula (II) can further have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Incorporation of isotopes into metal chelating effector groups, such as $^{64}$Cu, $^{67}$Ga, $^{68}$Ga, and $^{177}$Lu can be useful for visualizing tumour specific antigens employing PET or SPECT imaging.

Incorporation of isotopes into metal chelating effector groups, such as, but not limited to $^{90}$Y, $^{177}$Lu, and $^{213}$Bi, can present the option of targeted radiotherapy, whereby metal-chelator—bearing compounds of formula (II) carry the therapeutic radionuclide towards the target protein and site of action.

Isotopically-labeled compounds of formula (II) can generally be prepared by conventional techniques known to those skilled in the art or by processes analogous to those described in the accompanying Examples using an appropriate isotopically-labeled reagent in place of the non-labeled reagent previously employed.

Binding Activity

Specificity, in the context herein, refers to the ability of a ligand to bind or otherwise interact with its cognate target to the exclusion of entities which are similar to the target. For example, specificity can refer to the ability of a ligand to inhibit the interaction of a human enzyme, but not a homologous enzyme from a different species. Using the approach described herein, specificity can be modulated, that is increased or decreased, so as to make the ligands more or less able to interact with homologues or paralogues of the intended target. Specificity is not intended to be synonymous with activity, affinity or avidity, and the potency of the action of a ligand on its target (such as, for example, binding affinity or level of inhibition) are not necessarily related to its specificity.

Binding activity, as used herein, refers to quantitative binding measurements taken from binding assays, for example as described herein. Therefore, binding activity refers to the amount of peptide ligand which is bound at a given target concentration.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands can be capable of binding to two or more targets and are therefore multispecific. Suitably, they bind to two targets, and are dual specific. The binding may be independent, which would mean that the binding sites for the targets on the peptide are not structurally hindered by the binding of one or other of the targets. In this case, both targets can be bound independently. More generally, it is expected that the binding of one target will at least partially impede the binding of the other.

There is a fundamental difference between a dual specific ligand and a ligand with specificity which encompasses two related targets. In the first case, the ligand is specific for both targets individually, and interacts with each in a specific manner. For example, a first loop in the ligand may bind to a first target, and a second loop to a second target. In the second case, the ligand is non-specific because it does not differentiate between the two targets, for example by interacting with an epitope of the targets which is common to both.

In the context of the present invention, it is possible that a ligand which has activity in respect of, for example, a target and an orthologue, could be a bispecific ligand. However, in one embodiment the ligand is not bispecific, but has a less precise specificity such that it binds both the target and one or more orthologues. In general, a ligand which has not been selected against both a target and its orthologue is less likely to be bispecific due to the absence of selective pressure towards bispecificity. The loop length in the bicyclic peptide may be decisive in providing a tailored binding surface such that good target and orthologue cross-reactivity can be obtained, while maintaining high selectivity towards less related homologues.

If the ligands are truly bispecific, in one embodiment at least one of the target specificities of the ligands will be common amongst the ligands selected, and the level of that specificity can be modulated by the methods disclosed herein. Second or further specificities need not be shared, and need not be the subject of the procedures set forth herein.

A target is a molecule or part thereof to which the peptide ligands bind or otherwise interact with. Although binding is seen as a prerequisite to activity of most kinds, and may be an activity in itself, other activities are envisaged. Thus, the present invention does not require the measurement of binding directly or indirectly.

The molecular scaffold is any molecule which is able to connect the peptide at multiple points to impart one or more structural features to the peptide. Preferably, the molecular scaffold comprises at least three attachment points for the peptide, referred to as scaffold reactive groups. These groups are capable of reacting with the cysteine residues ($C_i$, $C_{ii}$ and $C_{iii}$) on the peptide to form a covalent bond. They do not merely form a disulphide bond, which is subject to reductive cleavage and concomitant disintegration of the molecule, but form stable, covalent thioether linkages. Preferred structures for molecular scaffolds are described below.

Molecular Scaffold

Molecular scaffolds are described in, for example, WO 2009/098450 and references cited therein, particularly WO 2004/077062 and WO 2006/078161.

As noted in the foregoing documents, the molecular scaffold may be a small molecule, such as a small organic molecule.

In one embodiment the molecular scaffold may be, or may be based on, natural monomers such as nucleosides, sugars, or steroids. For example the molecular scaffold may comprise a short polymer of such entities, such as a dimer or a trimer.

In one embodiment the molecular scaffold is a compound of known toxicity, for example of low toxicity. Examples of suitable compounds include cholesterols, nucleotides, steroids, or existing drugs such as tamazepam.

In one embodiment the molecular scaffold may be a macromolecule. In one embodiment the molecular scaffold is a macromolecule composed of amino acids, nucleotides or carbohydrates.

In one embodiment the molecular scaffold comprises reactive groups that are capable of reacting with functional group(s) of the polypeptide to form covalent bonds.

The molecular scaffold may comprise chemical groups which form the linkage with a peptide, such as amines, thiols, alcohols, ketones, aldehydes, nitriles, carboxylic acids, esters, alkenes, alkynes, azides, anhydrides, succinimides, maleimides, alkyl halides and acyl halides.

In one embodiment, the molecular scaffold may comprise or may consist of tris(bromomethyl)benzene, especially 1,3,5-tris(bromomethyl)benzene ('TBMB'), or a derivative thereof.

In one embodiment, the molecular scaffold is 2,4,6-tris (bromomethyl)mesitylene. This molecule is similar to 1,3, 5-tris(bromomethyl)benzene but contains three additional methyl groups attached to the benzene ring. This has the advantage that the additional methyl groups may form further contacts with the polypeptide and hence add additional structural constraint.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

Scaffold reactive groups that could be used on the molecular scaffold to react with thiol groups of cysteines are alkyl halides (or also named halogenoalkanes or haloalkanes).

Examples include bromomethylbenzene (the scaffold reactive group exemplified by TBMB) or iodoacetamide. Other scaffold reactive groups that are used to selectively couple compounds to cysteines in proteins are maleimides. Examples of maleimides which may be used as molecular scaffolds in the invention include: tris-(2-maleimidoethyl) amine, tris-(2-maleimidoethyl)benzene, tris-(maleimido) benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise.

Synthesis

The peptides of the formula (II) may be manufactured synthetically by standard solid phase peptide synthesis techniques followed by reaction with a molecular scaffold in vitro. When this is performed, standard chemistry may be used. This enables the rapid large scale preparation of soluble material for further downstream experiments or validation. Such methods could be accomplished using conventional chemistry such as that disclosed in Timmerman et al (supra).

Thus, the invention also relates to manufacture of polypeptides or conjugates selected as set out herein, wherein the manufacture comprises optional further steps as explained below. In one embodiment, these steps are carried out on the end product polypeptide/conjugate made by chemical synthesis.

Optionally amino acid residues in the polypeptide of interest may be substituted when manufacturing a conjugate or complex.

Peptides can also be extended, to incorporate for example another loop and therefore introduce multiple specificities.

To extend the peptide, it may simply be extended chemically at its N-terminus or C-terminus or within the loops or elsewhere using orthogonally protected lysines (and analogues) using standard solid phase or solution phase chemistry. Standard (bio)conjugation techniques may be used to introduce an activated or activatable N- or C-terminus. Alternatively additions may be made by fragment condensation or native chemical ligation e.g. as described in (Dawson et al. 1994. Synthesis of Proteins by Native Chemical Ligation. Science 266:776-779), or by enzymes, for example using subtiligase as described in (Chang et al Proc Natl Acad Sci USA. 1994 Dec. 20; 91(26):12544-8 or in Hikari et al Bioorganic & Medicinal Chemistry Letters Volume 18, Issue 22, 15 Nov. 2008, Pages 6000-6003).

Alternatively, the peptides may be extended or modified by further conjugation through disulphide bonds. This has the additional advantage of allowing the first and second peptide to dissociate from each other once within the reducing environment of the cell. In this case, the molecular scaffold (e.g. TBMB) could be added during the chemical synthesis of the first peptide so as to react with the three cysteine groups; a further cysteine or thiol could then be appended to the N or C-terminus of the first peptide, so that this cysteine or thiol only reacted with a free cysteine or thiol of the second peptide, forming a disulfide-linked bicyclic peptide-peptide conjugate.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. In one embodiment, the coupling is conducted in such a manner that it does not block the activity of either entity.

According to a further aspect of the invention, there is provided a process for preparing a drug conjugate as defined herein which comprises the synthetic route described in Scheme I.

Pharmaceutical Compositions

According to a further aspect of the invention, there is provided a pharmaceutical composition comprising a drug conjugate as defined herein in combination with one or more pharmaceutically acceptable excipients.

Generally, the drug conjugates will be utilised in purified form together with pharmacologically appropriate excipients or carriers. Typically, these excipients or carriers include aqueous or alcoholic/aqueous solutions, emulsions or suspensions, including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The drug conjugates of the present invention may be used as separately administered compositions or in conjunction with other agents. These can include antibodies, antibody fragments and various immunotherapeutic drugs, such as cylcosporine, methotrexate, adriamycin or cisplatinum and immunotoxins. Pharmaceutical compositions can include "cocktails" of various cytotoxic or other agents in conjunction with the drug conjugates of the present invention, or even combinations of drug conjugates according to the present invention having different specificities, such as those comprising polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the drug conjugates of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The drug conjugates of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that levels may have to be adjusted upward to compensate.

The compositions containing the present drug conjugates or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected drug conjugate per kilogram of body weight, with doses of 0.05 to 2.0 mg/kg/dose being more commonly used. For prophylactic applications, compositions containing the present drug conjugates or cocktails thereof may also be administered in similar or slightly lower dosages.

A composition containing a drug conjugate according to the present invention may be utilised in prophylactic and therapeutic settings to aid in the alteration, inactivation, killing or removal of a select target cell population in a mammal. In addition, the drug conjugates described herein may be used extracorporeally or in vitro selectively to kill, deplete or otherwise effectively remove a target cell population from a heterogeneous collection of cells. Blood from a mammal may be combined extracorporeally with the selected drug conjugates whereby the undesired cells are killed or otherwise removed from the blood for return to the mammal in accordance with standard techniques.

Therapeutic Uses

The bicyclic peptides of formula (II) have specific utility as high affinity binders of membrane type 1 metalloprotease (MT1-MMP, also known as MMP14). MT1-MMP is a transmembrane metalloprotease that plays a major role in the extracellular matrix remodeling, directly by degrading several of its components and indirectly by activating pro-MMP2. MT1-MMP is crucial for tumor angiogenesis (Sounni et al (2002) FASEB J. 16(6), 555-564) and is over-expressed on a variety of solid tumours, therefore the drug conjugates comprising MT1-MMP-binding bicycle peptides of the present invention have particular utility in the targeted treatment of cancer, in particular solid tumours such as non-small cell lung carcinomas. In one embodiment, the bicyclic peptide of formula (II) is specific for human MT1-MMP. In a further embodiment, the bicyclic peptide of formula (II) is specific for mouse MT1-MMP. In a yet further embodiment, the bicyclic peptide of formula (II) is specific for human and mouse MT1-MMP. In a yet further embodiment, the bicyclic peptide of formula (II) is specific for human, mouse and dog MT1-MMP.

Polypeptide ligands of formula (II) may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The conjugates of the peptide ligands of the present invention will typically find use in preventing, suppressing or treating cancer, in particular solid tumours such as non-small cell lung carcinomas.

Thus, according to a further aspect of the invention, there are provided drug conjugates of the peptide ligand as defined herein for use in preventing, suppressing or treating cancer, in particular solid tumours such as non-small cell lung carcinomas.

According to a further aspect of the invention, there is provided a method of preventing, suppressing or treating cancer, in particular solid tumours such as non-small cell lung carcinomas which comprises administering to a patient in need thereof a drug conjugate of the peptide ligand as defined herein.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the drug conjugates in protecting against or treating the disease are available. The use of animal model systems is facilitated by the present invention, which allows the development of polypeptide ligands which can cross react with human and animal targets, to allow the use of animal models.

The invention is further described below with reference to the following examples.

EXAMPLES

Materials and Methods
Protein Expression

The MT1-MMP hemopexin-like repeats (also known as the MT1-MMP hemopexin domain), residues Cys319-Gly511 from the human gene, were transiently expressed in HEK293 cells as secreted N-terminally His6-tagged soluble protein, using the pEXPR-IBA42 (IBA) expression vector. Following expression, the protein was purified by Nickel-NTA affinity chromatography followed by gel filtration, and purity was checked by SDS-PAGE. Batch to batch variability was also monitored by fluorescence thermal shift experiments in the presence/absence of a hemopexin domain binding bicycle.

Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with the following side chain protecting groups: Arg(Pbf); Asn(Trt); Asp(OtBu); Cys(Trt); Glu(OtBu); Gln(Trt); His(Trt); Lys(Boc); Ser(tBu); Thr(tBu); Trp(Boc); and Tyr(tBu) (Sigma). The coupling reagent was HCTU (Pepceuticals), diisopropylethylamine (DIPEA, Sigma) was employed as a base, and deprotection was achieved with 20% piperidine in DMF (AGTC). Syntheses were performed using 0.37 mmol/gr Fmoc-Rink amide AM resin (AGTC), Fmoc-amino acids were utilised at a four-fold excess, and base was at a four-fold excess with respect to the amino acids. Amino acids were dissolved at 0.2M in DMSO, HCTU at 0.4M in DMF, and DIPEA at 1.6M in N-methylpyrrolidone (Alfa Aesar). Conditions were such that coupling reactions contained between 20 to 50% DMSO in DMF, which reduced aggregation and deletions during the solid phase synthesis and enhanced yields. Coupling times were generally 30 minutes, and deprotection times 2×5 minutes. Fmoc-N-methylglycine (Fmoc-Sar-OH, Merck) was coupled for 1 hr, and deprotection and coupling times for the following residue were 20 min and 1 hr, respectively. After synthesis, the resin was washed with dichloromethane, and dried. Cleavage of side-chain protecting groups and from the support was effected using 10 mL of 95:2.5:2.5:2.5 v/v/v/w TFA/H$_2$O/iPr$_3$SiH/dithiothreitol for 3 hours. Following cleavage, the spent resin was removed by filtration, and the filtrate was added to 35 mL of diethylether that had been cooled at −80° C. Peptide pellet was centrifuged, the etheric supernatant discarded, and the peptide pellet washed with cold ether two more times. Peptides were then resolubilised in 5-10 mL acetonitrile-water and lyophilised. A small sample was removed for analysis of purity of the crude product by mass spectrometry (MALDI-TOF, Voyager DE from Applied Biosystems). Following lyophilisation, peptide powders were taken up in 10 mL 6 M guanidinium hydrochloride in H$_2$O, supplemented with 0.5 mL of 1 M dithiothreitol, and loaded onto a C8 Luna preparative HPLC column (Phenomenex). Solvents (H$_2$O, acetonitrile) were acidified with 0.1% heptafluorobutyric acid. The gradient ranged from 30-70% acetonitrile in 15 minutes, at a flowrate of 15-20 mL/min, using a Gilson preparative HPLC system. Fractions containing pure linear peptide material (as identified by MALDI) were combined, and modified with 1,3,5-tris(bromomethyl)benzene (TBMB, Sigma). For this, linear peptide was diluted with H$_2$O up to ~35 mL, ~500 μL of 100 mM TBMB in acetonitrile was added, and the reaction was initiated with 5 mL of 1 M NH$_4$HCO$_3$ in H$_2$O. The reaction was allowed to proceed for ~30-60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20° C. for storage.

All amino acids, unless noted otherwise, were used in the L-configurations.

Non-natural amino acids were incorporated into peptide sequence using the general methods described above.

The list of non-natural amino acid precursors employed herein are summarised in the table below:

| Supplier | Short name | Full chemical name |
|---|---|---|
| AGTC | D-Asp | Fmoc-D-Asp(tBu)-OH |
| Iris Biotech | HPhe | Fmoc-L-Homophenylalanine |
| Alfa Aesar | 5FPhe | Fmoc-pentafluoro-L-phenylalanine |
| PolyPeptide Gropu | 4BrPhe | Fmoc-4-bromo-L-phenylalanine |
| Iris Biotech | bAla | Fmoc-beta-Ala-OH |
| Iris Biotech | 3Pal | Fmoc-L-3Pal-OH |
| Iris Biotech | 4Pal | Fmoc-L-4Pal-OH |
| Iris Biotech | D-Pro | Fmoc-D-Pro-OH |
| Merck Novabiochem | Aib | Fmoc-Aib-OH |
| Merck Novabiochem | D-Ala | Fmoc-D-Ala-OH |
| Merck Novabiochem | D-Arg | Fmoc-D-Arg(Pbf)-OH |
| Merck Novabiochem | D-Gln | Fmoc-D-Gln(Trt)-OH |
| Merck Novabiochem | D-His | Fmoc-D-His(Trt)-OH |
| Merck Novabiochem | Hyp | Fmoc-Hyp(tBu)-OH |
| Merck Novabiochem | D-Leu | Fmoc-D-Leu-OH |
| Merck Novabiochem | HArg | Fmoc-L-HArg(Boc)2-OH |
| Peptech Corporation | 4,4-BPAl | Fmoc-L-4,4'-Biphenylalanine |
| Peptech Corporation | 3,3-DPA | Fmoc-L-3,3-Diphenylalanine |
| Peptech Corporation | Dpg | Fmoc-Dipropylglycine |
| Peptech Corporation | 1Nal | Fmoc-L-1-Naphthylalanine |
| Peptech Corporation | 2NAl | Fmoc-L-2-Naphthylalanine |
| Peptech Corporation | Pip | Fmoc-L-Pipecolic acid |
| Polypeptide Group | Aze | Fmoc-L-azetidine-2-carboxylic acid |
| Polypeptide Group | Cha | Fmoc-beta-cyclohexyl-L-alanine |
| Polypeptide Group | 4FluoPro | (2S,4R)-Fmoc-4-fluoro-pyrrolidine-2-carboxylic acid |
| AGTC | D-Asp | Fmoc-D-Asp(tBu)-OH |
| Merck | tBuGly | Fmoc-α-tert-butylglycine |
| Iris Biotech | Chg | Fmoc-L-cyclohexylglycine |
| Fluorochem | Phg | Fmoc-Phenylglycine-OH |
| Iris Biotech | 3Pal | Fmoc-L-3Pal-OH |
| Iris Biotech | 4Pal | Fmoc-L-4Pal-OH |
| Merck Novabiochem | D-Leu | Fmoc-D-Leu-OH |
| Merck Novabiochem | HArg | Fmoc-L-HArg(Boc)2-OH |
| Polypeptide Group | 3,4 DCPhe | Fmoc-3,4-dichloro-L-phenylalanine |
| Polypeptide Group | Cha | Fmoc-beta-cyclohexyl-L-alanine |

Peptides used for the pharmacokinetic studies were lyophilised from 0.1% TFA in water to afford the TFA salts or free acids of the compounds.

Synthesis of BT17BDC-27 and BT17BDC-28 Using 17-69-07-N268 and 17-69-07-N241 as Precursor Bicyclic Peptides The precursor peptides 17-69-07-N241 and 17-69-07-N268 have the sequences (bAla)-Sar10-AC(D-Ala)NE(1Nal)(D-Ala)CEDFYD(tBuGly)C and AC(D-Ala)NE(1Nal)(D-Ala)CEDFYD(tBuGly)C, respectively. Both are cyclised with TBMB as previously disclosed, contain a unique amino group at the N-terminus that is used as a conjugation site, and are amidated C-terminally.

The synthetic scheme is shown below:

Scheme I

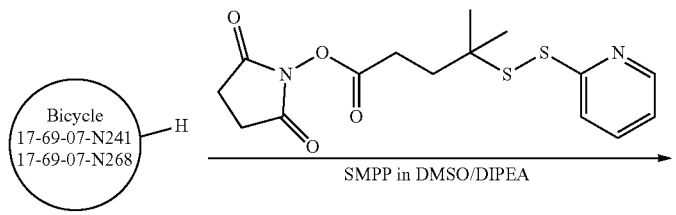

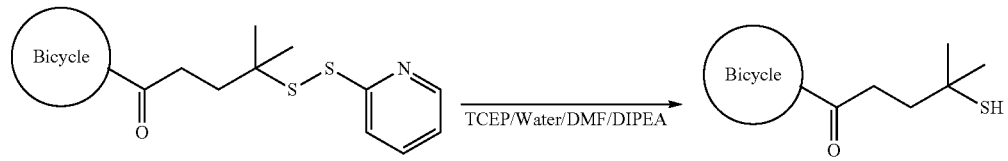

17-69-07-319
17-69-07-331

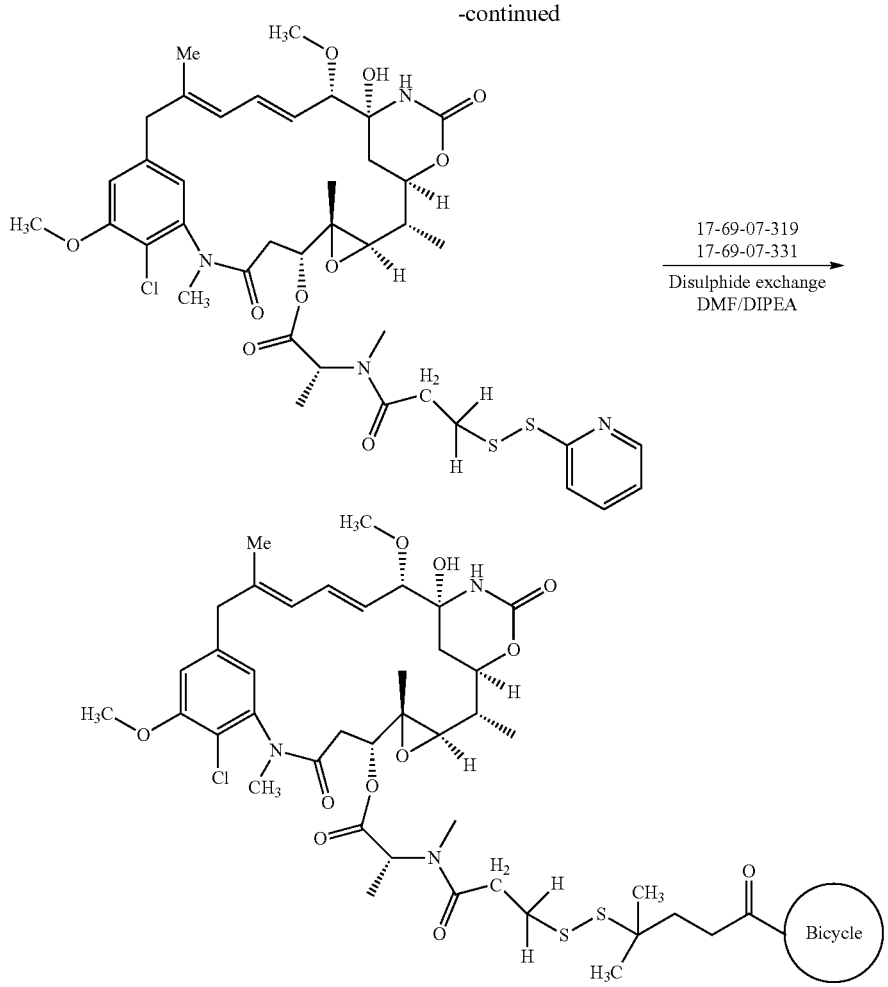

BT17BDC-28 (derived from 17-69-07-N241
BT17BDC-27 (derived from 17-69-07-N268

The molecular weights of the precursors, and intermediate thiol peptides, are shown in Table 1 below:

TABLE 1

Molecular Properties of BT17BDC-27 and BT17BDC-28

| BDC | Molecular weight | Reactive thiol Bicycle Precursor | Molecular Weight | Bicycle Precursor | Molecular weight |
|---|---|---|---|---|---|
| BT17BDC-27 | 2742.567 | 17-69-07-N331 | 2007.30 | 17-69-07-N268 | 1877.08 |
| BT17BDC-28 | 3524.427 | 17-69-07-N319 | 2789.16 | 17-69-07-N241 | 2658.95 |

Synthesis of 17-69-07-N331

2.1 mL of 20.1 mM Bicycle solution (17-69-07-N268) in DMSO (0.042 mmol, 80 mg) were added to 0.6 mL of 94.0 mM SMPP NHS ester solution (CAS Nr: 890409-85-5) in anhydrous DMSO (0.0546 mmol), followed by addition of 154 μL of neat DIPEA (0.884 mmol) and the resulting mixture was stirred at room temperature. After 1.5 hour, the reaction was sampled and analysed by LCMS and the reaction was judged complete.

423 μL of 200 mM TCEP solution (tris(2-carboxyethyl) phosphine neutralised with ammonium bicarbonate to pH ~8) (0.0846 mmol) at room temperature was directly added to the reaction mixture. After 30 min the reduction reaction was sampled and judged complete by LCMS.

For purification, the solution (~3.0 mL) was diluted and purified by AKTA purifier 100 equipped with a C18 column (YMC-Actus Triart C18 Preparative HPLC column, 12 nm, 10 μm, 250×50.0 mm) (YMC) (35×200 mm) using water (0.1% TFA) and acetonitrile (0.1% TFA) as mobile phases. The gradient was 35-65% acetonitrile over 20 minutes at a flow rate of 100 mL/min. The fractions containing the product (judged by UV and selected by purity as determined by LCMS) were combined together and lyophilised, giving the 73 mg of pure 17-69-07-N331 (83% yield).

Synthesis of 17-69-07-N319

Conditions and purification were as with 17-69-07-N331, starting from 0.219 mmol (583 mg) 17-69-07-N241, affording 417 mg of 17-69-07-N319 (68% yield).

Synthesis of DM1-S-S-Py

Dithiopyridine (341 mg, 1.55 mmol) was added to a solution of DM1-SH (229 mg, 0.31 mmol) in anhydrous DMF (12.43 ml) with DIPEA (531 μl, 3.1 mmol). The reaction was mixed and left at room temperature for 1.5 hours; the reaction progress was assessed by ESI MS. ESI MS confirmed the product had formed MZ 847.3 Da and that the starting material had been consumed. The product was purified using a Phenomenex Luna C18 preparative column with 0.1% TFA containing mobile phases, on a 20-80% acetonitrile gradient over 9 column volumes. The reaction mixture was diluted into acetonitrile and then diluted with water (final acetonitrile concentration 20%, final 4% DMF). Fractions that were >95% purity by analytical reverse phase HPLC were pooled. The product (DM1-S-S-Py) was quantified by UV absorbance at 280 nm (e=5935 Mcm-1) in 1:1 MeCN:water, yielding an isolated 185 mg (70% yield).

Synthesis of BT17BDC-27

Peptide 17-69-07-N331 (239 mg, 119 mmol) was dissolved to a concentration of 30 mM in anhydrous DMF with DIPEA (123 ml, 59 mmol). DM1-S-S-Pyridyl (60 mg, 71 mmol) was also dissolved in anhydrous DMF to a concentration of 25 mM. The DM1-S-S-Pyridyl solution was added to the peptide solution and mixed. The reaction progress was analysed after 1 hour by HPLC and MS. Total reaction time was 2 hours. The reaction mixture was diluted into a solution of 20% acetonitrile/water, to a final DMF concentration of 2%. The crude reaction mixture was purified using a Phenomenex Luna C18 preparative column with 0.1% TFA containing mobile phases, on 20-90% acetonitrile gradient over 9 column volumes. 190 mg purified peptide >95% was obtained from two reactions, with a total peptide input of 461 mg (yield 36.2%). The peptide was quantified using the absorbance measured at 280 nm (e=13225 Mcm-1).

Synthesis of BT17BDC-28

Peptide 17-69-07-N319 (206 mg, 74 mmol) was dissolved to a concentration of 30 mM in anhydrous DMF with DIPEA (100 ml, 59 mmol). DM1-S-S-Pyridyl (50 mg, 59 mmol) was also dissolved in anhydrous DMF to a concentration of 25 mM. The DM1-S-S-Pyridyl solution was added to the peptide solution and mixed. The reaction progress was analysed after 1 hour by HPLC and MS. Total reaction time was 3 hours. The reaction mixture was diluted into acetonitrile then diluted into water, final DMF concentration of 4%, acetonitrile 20%. The reaction mixture was filtered before purification by RP-HPLC. The crude reaction mixture was purified as described above, and 230 mg purified peptide >95% was obtained from two reactions, with a total peptide input of 395 mg (yield 55.3%). The conjugate was quantified using the absorbance measured at 280 nm (e=13225 Mcm-1) in 50 mM HEPES pH 7.5.

Dissociation Rate Constant Determination of Bicyclic Binders to MT1-MMP

Direct Binding Fluorescence Polarisation (Anisotropy) Assays

Direct Binding Fluorescence Polarisation or Anisotropy Assays are performed by titrating a constant concentration of fluorescent tracer (here, the fluoresceinated bicyclic peptide to be studied) with its binding partner (here, the MT1-MMP hemopexin domain). As the concentration of binding partner increases during the titration, the polarisation signal changes in proportion to the fraction of bound and unbound material. This allows determination of dissociation rates (Kd) quantitatively. Assay data can be fit using standard ligand binding equations.

Typically, concentrations of the tracer are ideally well below the Kd of the tracer:titrant pair, and concentrations chosen are usually at ~1 nM or less. The titrant (binding partner) concentration is varied from 0.1 nM up to typically 5 µM. The range is chosen such that the maximum change in fluorescence polarisation can be observed. Buffers employed are phosphate buffered saline in the presence of 0.01% Tween. Experiments were run in black 384 well low-bind/low volume plates (Corning 3820), and the fluorescent polarisation signal was measured using a BMG Pherastar FS plate reader.

Fluorescent tracers referred to in the text are bicyclic peptides that have been fluoresceinated using 5,6-carboxyfluorescein. Fluoresceination may be performed on the N-terminal amino group of the peptide, which is separated from the bicycle core sequence by a sarcosine spacer (usually Sar5). This can be done during Fmoc solid phase synthesis or post-synthetically (after cyclisation with TBMB and purification) if the N-terminal amino group is unique to the peptide. Fluoresceination can also be performed on the C-terminus, usually on a Lysine introduced as the first C-terminal residue, which is then separated from the bicycle core sequence by a sarcosine spacer (usually Sar6). Thus, N-terminal tracers can have a molecular format described as Fluo-Gly-Sar5-A(BicycleCoreSequence), and (BicycleCoreSequence)-A-Sar6-K(Fluo) for a C-terminally fluoresceinated construct. Fluorescent tracers used in the Examples are A-(17-69)-A-Sar6-K(Fluo), A-(17-69-07)-A-Sar6-K(Fluo), and A-(17-69-12)-A-Sar6-K(Fluo). Due to the acidic nature of the 17-69 fluorescent peptides, they were typically prepared as concentrated DMSO stocks, from which dilution were prepared in 100 mM Tris pH 8 buffer.

Competition Assays Using Fluorescence Polarisation (Anisotropy)

Due to their high affinities to the MT1-MMP Hemopexin domain (PEX), the fluoresceinated derivatives of 17-69-07 and 17-69-12 (denoted as 17-69-07-N040 and 17-69-12-N005, respectively) can be used for competition experiments (using FP for detection). Here, a pre-formed complex of PEX with the fluorescent PEX-binding tracer is titrated with free, non-fluoresceinated bicyclic peptide. Since all 17-69-based peptides are expected to bind at the same site, the titrant will displace the fluorescent tracer from PEX. Dissociation of the complex can be measured quantitatively, and the Kd of the competitor (titrant) to the target protein determined. The advantage of the competition method is that the affinities of non-fluoresceinated bicyclic peptides can be determined accurately and rapidly.

Concentrations of tracer are usually at the Kd or below (here, 1 nM), and the binding protein (here, hemopexin of MT1-MMP) is at a 15-fold excess such that >90% of the tracer is bound. Subsequently, the non-fluorescent competitor bicyclic peptide (usually just the bicycle core sequence) is titrated, such that it displaces the fluorescent tracer from the target protein. The displacement of the tracer is measured and associated with a drop in fluorescence polarisation. The drop in fluorescence polarisation is proportional to the fraction of target protein bound with the non-fluorescent titrant, and thus is a measure of the affinity of titrant to target protein.

The raw data is fit to the analytical solution of the cubic equation that describes the equilibria between fluorescent tracer, titrant, and binding protein. The fit requires the value of the affinity of fluorescent tracer to the target protein, which can be determined separately by direct binding FP experiments (see previous section). The curve fitting was performed using Sigmaplot 12.0 and used an adapted version of the equation described by Zhi-Xin Wang (FEBS Letters 360 (1995) 111-114).

Plasma Stability Profiling

Method #1:

A rapid plasma stability profiling assay was developed that employed mass spectrometric detection (MALDI-TOF, Voyager DE, Applied Biosystems) of the parent mass as well as plasma-protease induced fragments thereof. By assessing the nature of the fragments, preferred cleavage sites can be determined. Here, a 1-1.5 mM peptide stock (in DMSO) was directly diluted into mouse/rat/human plasma (Sera labs, using citrate as anticoagulant), giving a final concentration of 50 μM peptide, and incubated for up to 48 hrs at 37° C. 5 μL samples were taken at appropriate time points and frozen at −80° C. For analysis, the samples were defrosted, mixed with 25 μL of 3:3:1 acetonitrile:methanol:water, and centrifuged at 13 k for 5 min. 5 μL of the peptide-containing supernatant was aspirated and mixed with 30 mM ammonium bicarbonate in a 1:1 mixture of acetonitrile:$H_2O$. 1 μL of this was then spotted on the MALDI plate, dried, and Matrix (alpha-cyanocinnamic acid, Sigma, prepared as a saturated solution in 1:1 acetonitrile:water containing 0.1% trifluoroacetic acid) was layered over the sample (1 μL), dried and analysed using the MALDI TOF. It should be noted that this is a qualitative assay serves to detect comparative changes in plasma stability between different bicycle peptide sequences, and functions as an excellent tool to determine preferred cleavage sites.

Method #2

To obtain plasma stability of bicyclic peptides quantitatively, peptide stock solutions (160 μM in DMSO) were mixed with plasma (human, rat or mouse), such that final concentrations were 4 μM, and incubated at 37° C. 40 μL samples were taken periodically up to 24 hrs and frozen at −80° C. Prior to LC-MS analysis, samples were defrosted, and mixed with 3 volumes (here, 120 μL) of 1 part water, 3 parts acetonitrile and 3 parts methanol. The milky suspensions were centrifuged for 40 min at 14000 rpm in a cooled centrifuge, and peptide-containing supernatants were quantitated for doubly/triply charged species and MS/MS fragments thereof using a Waters Xevo TQ-D instrument, while using a plasma extracted standard curve of the same peptides as a reference. The half-life of degradation in plasma was used to assess the comparative stability of the molecules.

Efficacy of BT17BDC-27 and BT17BDC-28 in EBC-1 Xenograft Mice.

Balb/c nude mice bearing subcutaneous EBC-1 xenograft tumours were treated with BDCs or vehicle. BDCs were dosed 3 times weekly for 2 weeks, dosing initiated when tumours measured approx. 150-200 mm³. Mice were monitored, and measurements of tumour volume and body weight recorded 3 times a week.

Example 1: Affinity Analysis of BT17BDC-27 and BT17-BDC-28

Two DM1-toxin BDCs were prepared (referred to hereinbefore as BT17BDC-27 and BT17BDC-28), whereby identical hindrance was introduced on the Bicycle side of the molecular construct. The hindering groups are methyl groups which are situated at the $R^3$ and $R^4$ positions.

BT17BDC-28 employs the bicyclic peptide 17-69-07-N241, which contains the bAla-Sar10 molecular spacer N-terminally attached to the Bicyclic peptide containing the 4 modifications (D-Ala1 1Nal4 D-Ala5 tBuGly11).

BT17BDC-27 employs the bicyclic peptide 17-69-07-N268, which lacks the bAla-Sar10 molecular spacer N-terminally attached to the Bicyclic peptide of 17-69-07-N241, while containing the same 4 modifications (D-Ala1 1Nal4 D-Ala5 tBuGly11).

The Bicyclic peptide sequences of 17-69-07-N241 and 17-69-07-N268, and their affinities to the MT1-MMP as determined by fluorescence polarisation competition experiments, are shown in Table 2:

TABLE 2

Binding Affinities of 17-69-07-N241 and 17-69-07-N268

| Peptide code | Molecular Description | Kd (nM) |
|---|---|---|
| 17-69-07-N241 | bAla-Sar10-A-(17-69-07) D-Ala1 1Nal4 D-Ala5 tBuGly11 | 1.21 ± 0.24 |
| 17-69-07-N268 | A-(17-69-07) D-Ala1 1Nal4 D-Ala5 tBuGly11 | 1.70 ± 0.28 |

From the data it is clear that the bAla-Sar10 molecular spacer is not required for retention of affinity to the target, and thus, conjugation with an effector (here, DM1) is conceivably tolerated. Furthermore, the BDC lacking the hydrophilic molecular Sar10 spacer has a lower molecular weight and higher toxin to weight ratio, and greater overall hydrophobicity which in concert may influence pharmacokinetic and pharmacodynamic behaviour.

BT17BDC-27 and BT17BDC-28 were synthesised according to Scheme I. Here, the amine-containing Bicyclic peptide precursors (17-69-07-N268 and 17-69-07-N241 respectively) were conjugated with SMPP (which introduces the pyridyl-disulphide-protected hindered disulphide), and reduced to reveal the free but hindered thiol on the Bicyclic peptide. This was then disulphide exchanged with pyridyl-disulfide activated DM1 (DM1-S-S-Py) to afford the desired products.

Example 2: In Vitro Characterisation of BT17BDC-27 and BT17BDC-28

Both BDC conjugate structures were assessed for several in vitro parameters such as retention of potency to the human MT1-MMP hemopexin domain, stability in mouse, rat and human plasma, and stability to reducing agents such as dithiothreitol.

The data is summarised in Table 3 below:

TABLE 3

In vitro properties of BT17BDC-27 and BT17BDC-28

| Bicycle Drug Conjugate | Kd (nM) (Hemopexin domain)[a] | $t_{1/2}$ (hrs) (human plasma)[b] | $t_{1/2}$ (hrs) (mouse plasma)[b] | $t_{1/2}$ (hrs) (rat plasma)[b] | Relative Stability to DTT (ADC)[c] | Relative Stability to DTT (BDC)[d] |
|---|---|---|---|---|---|---|
| BT17BDC-27 | 0.69 ± 0.26 (n = 2) | 36 | 23 | 9 | 14 | 32 |
| BT17BDC-28 | 1.65 ± 1.08 (n = 2) | 29 | 19 | 13 | 14 | 28 | where n = numbers of repeats

[a] determined by fluorescence polarisation competition experiments using 17-69-07-N040 as a tracer

[b] determined using quantitative LC-MS. Incubation time up to 24 hrs in plasma, containing 4 μM BDC.

[c] from Kellogg et al (2011) Bioconjugate Chemistry, 22, 717. Note these values relate to antibody drug conjugates containing the disulphide linker described in the text

[d] determined by quantitative LC-MS. Note these values relate to Bicycle Drug Conjugates containing the disulphide linker described in the text. Methods were adapted from Kellogg et al (2011) Bioconjugate Chemistry, 22, 717.

The data indicate that the constructs tolerate the toxin attachment, even in the absence of the Sar10 molecular spacer, as the affinities to the MT1-MMP target are retained. Furthermore, the relative stability to DTT compared to unhindered disulphide BDCs is virtually identical for both BT17BDC-27 and BT17BDC-28, indicating that the presence or absence of the molecular spacer does not impact the toxin release rate.

Example 3: In Vivo Efficacy of BT17BDC-27 and BT17BDC-28

Both BDCs were tested for their efficacies in in vivo mouse xenograft models, using the human lung squamous cell carcinoma line EBC-1.

Figure 2:
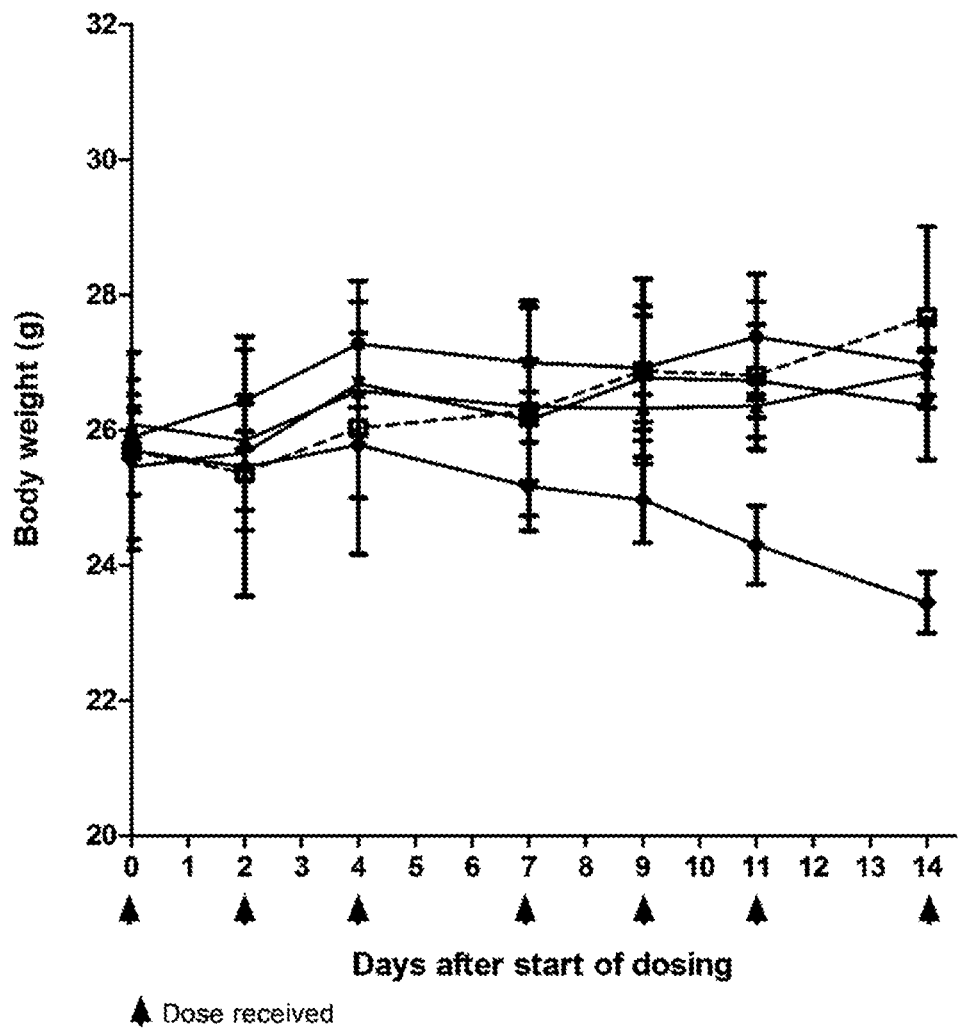
FIG. 2: Body weight during treatment of EBC-1 xenograft mice with BT17BDC-27, which is indicative of drug-associated toxicology and overall animal health.
Figure 3:
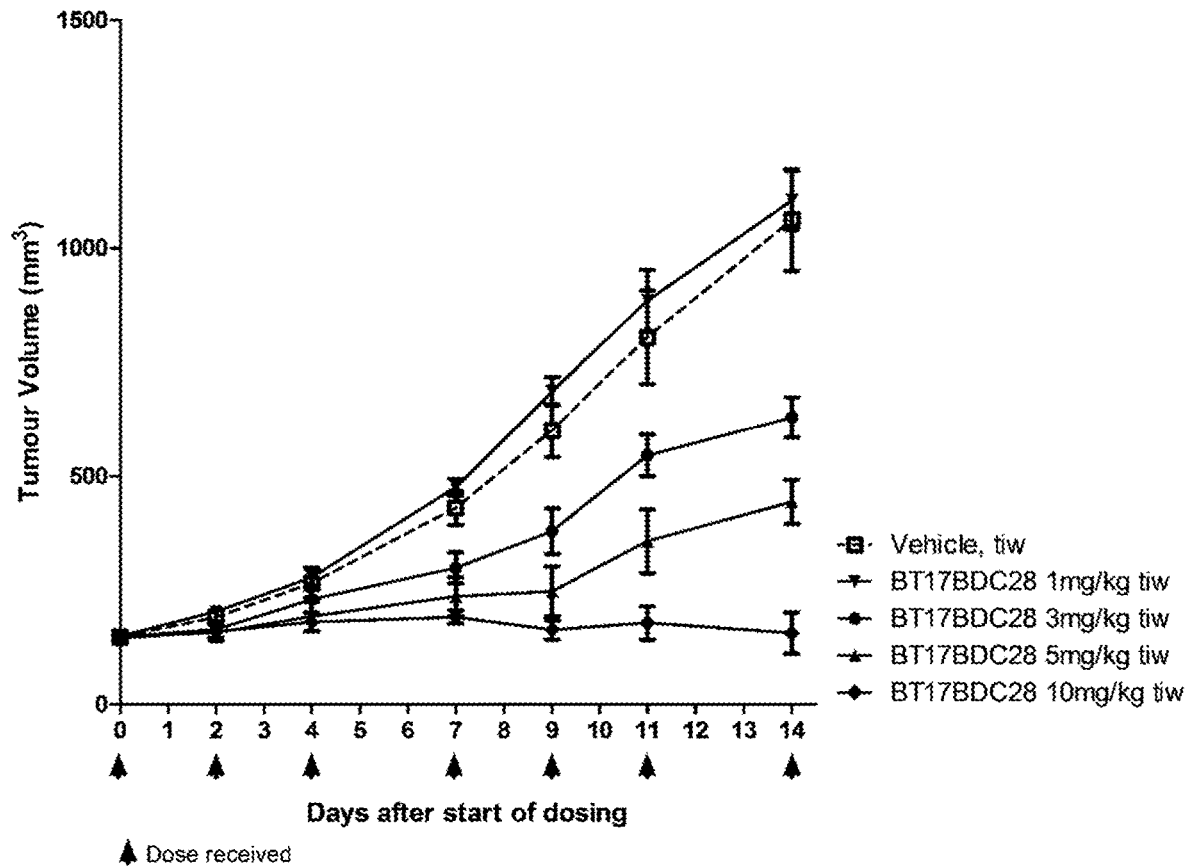
FIG. 3: Plot of mean tumour volume versus time for BT17BDC-28 in EBC-1 xenograft mice. Doses were administered on day 0, 2, 4, 7, 9, 11 and 14.
Figure 4:
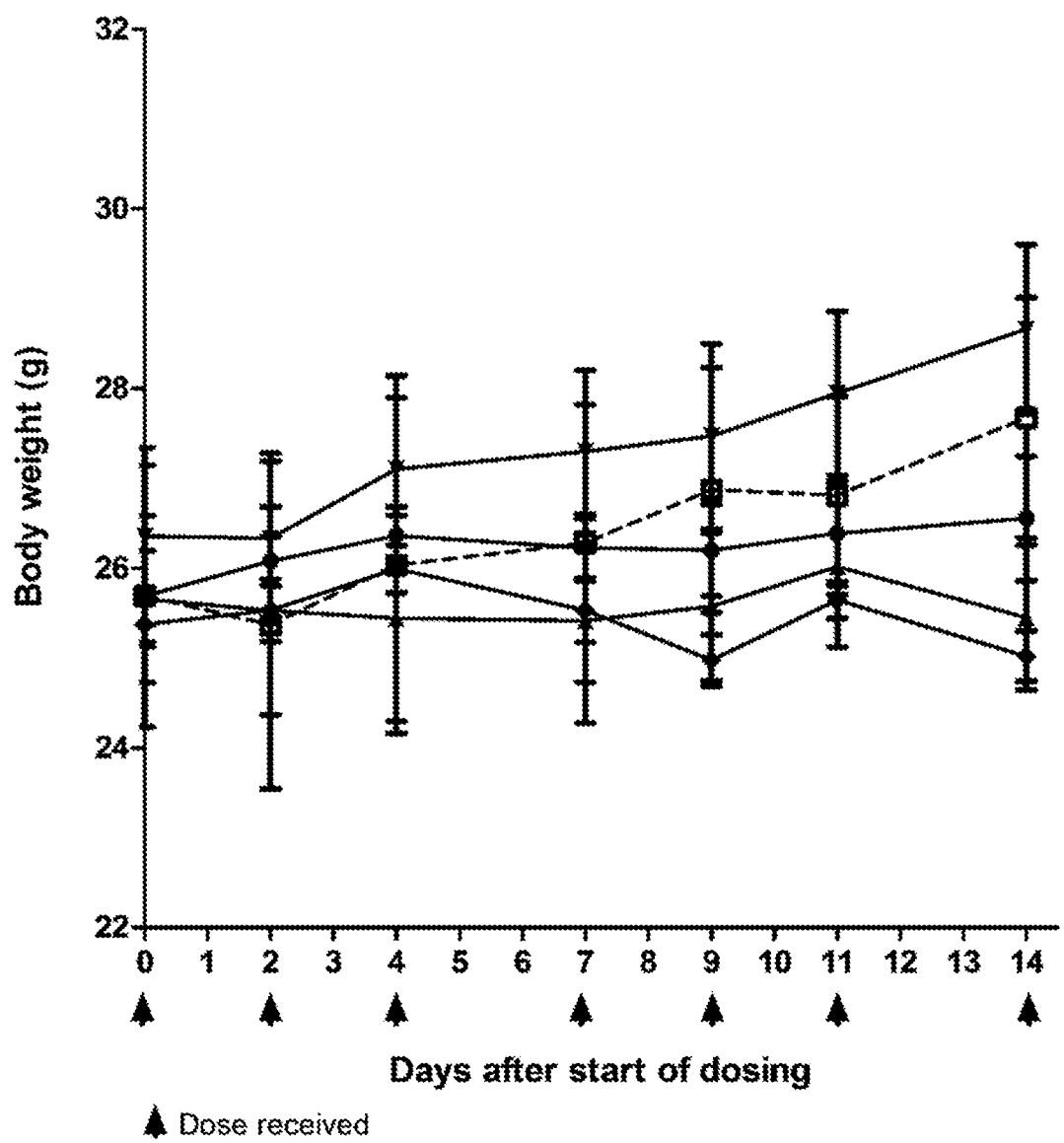
FIG. 4: Body weight during treatment of EBC-1 xenograft mice with BT17BDC-28, which is indicative of drug-associated toxicology and overall animal health.

BT17BDC-27 was more efficacious than BT17BDC-28, as it cleared tumours within 14 days (FIG. 1) at 10 mg/kg. A slight reduction in body weight was observable at this dose (FIG. 2). Conversely, at 10 mg/kg, BT17BDC-28 led to tumour growth stasis but not active regression (FIG. 3) while no weight loss was observed for BT17BDC-28 (FIG. 4). BT17BDC-27 merits further attention due to appreciable efficacy and tolerability at doses equal or lower than 5 mg/kg.

The invention claimed is:

1. A drug conjugate selected from

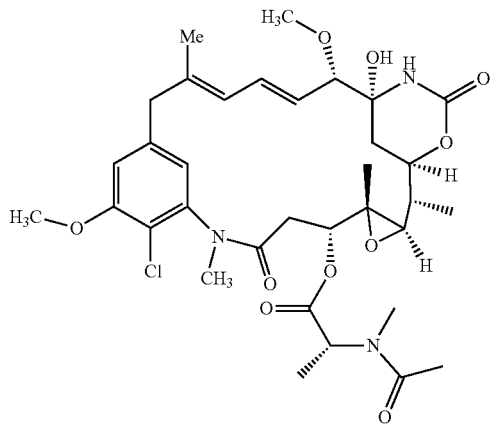

BT17BDC-27:

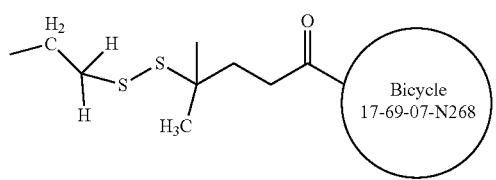

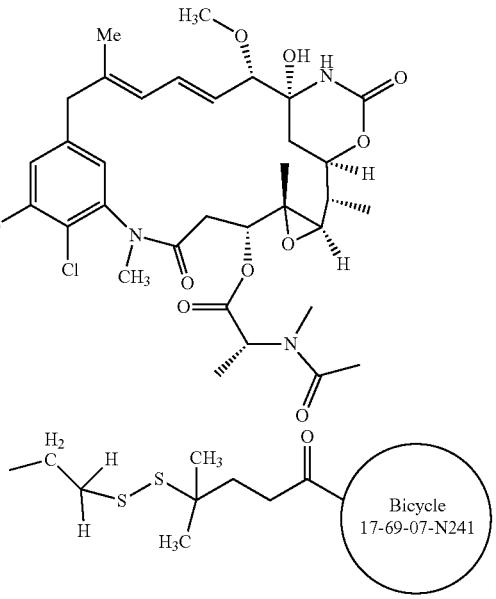

BT17BDC-28:

or a pharmaceutically acceptable salt thereof, wherein:

Bicycle 17-69-07-N268 represents -AC$_i$(D-Ala)NE(1Nal)(D-Ala)C$_{ii}$EDFYD(tBuGly)C$_{iii}$-CONH$_2$;

Bicycle 17-69-07-N241 represents -(bAla)-Sar10-AC$_i$(D-Ala)NE(1Nal)(D-Ala)C$_{ii}$EDFYD(tBuGly)C$_{iii}$-CONH$_2$;

C$_i$, C$_{ii}$ and C$_{iii}$ represent first, second and third cysteine residues, respectively; and each of Bicycle 17-69-07-N268 and 17-69-07-N241 is cyclised on C$_i$, C$_{ii}$, and C$_{iii}$ with 1,3,5-tris(bromomethyl)benzene) (TBMB) yielding a tri-substituted 1,3,5-trismethylbenzene structure.

2. A process for preparing the drug conjugate according to claim 1, or a pharmaceutically acceptable salt thereof, which comprises the synthetic route:

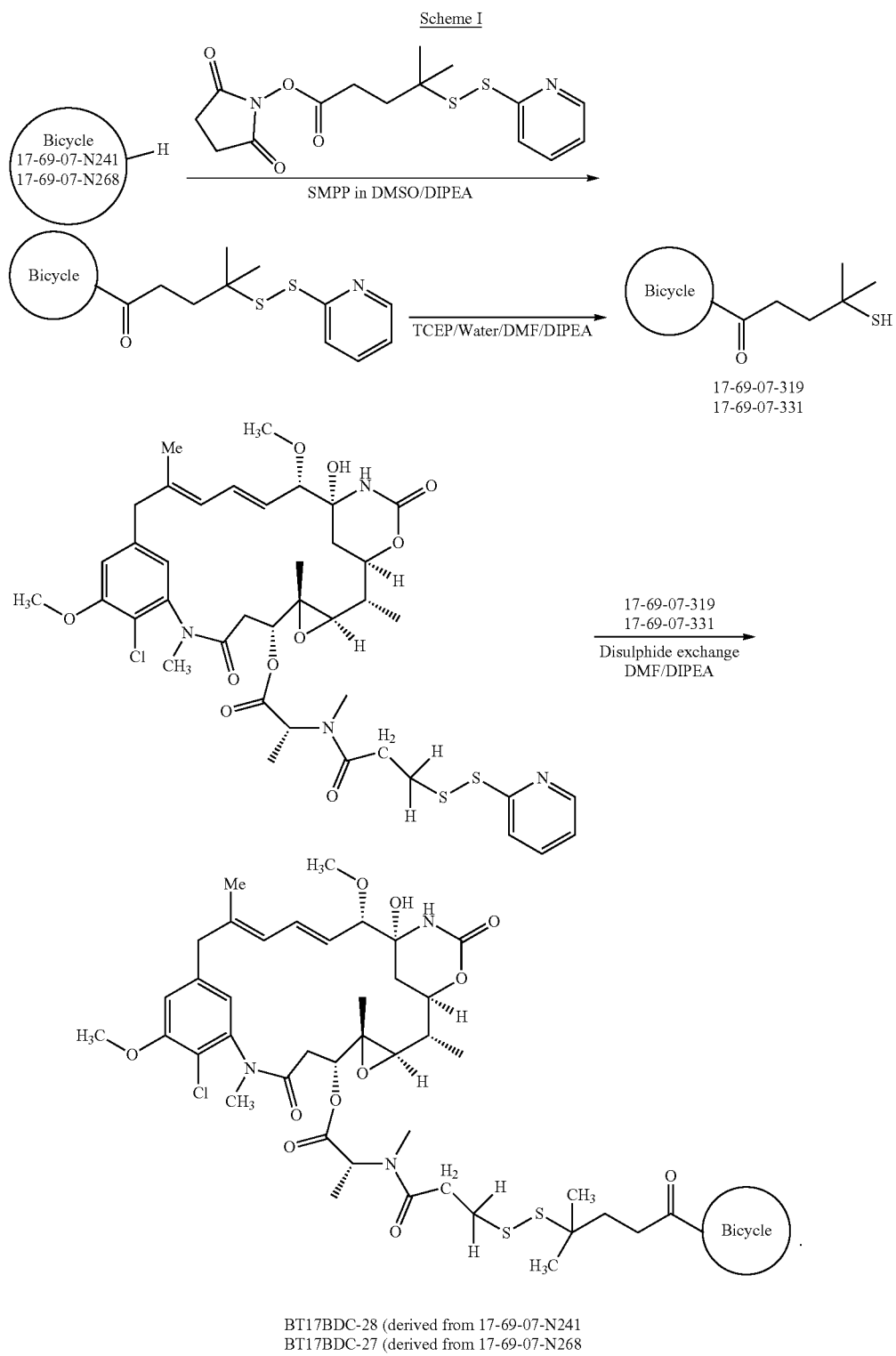

Scheme I

BT17BDC-28 (derived from 17-69-07-N241
BT17BDC-27 (derived from 17-69-07-N268

3. A pharmaceutical composition which comprises the drug conjugate of claim 1, or a pharmaceutically acceptable salt thereof, in combination with one or more pharmaceutically acceptable excipients.

4. A method of preventing, suppressing or treating cancer, comprising administering to a patient in need thereof the drug conjugate of claim 1, or a pharmaceutically acceptable salt thereof.

5. The method according to claim 4, wherein the cancer is a solid tumour.

6. The method according to claim 5, wherein the solid tumour is non-small cell lung carcinomas.

7. The drug conjugate according to claim 1, which is BT17BDC-27:

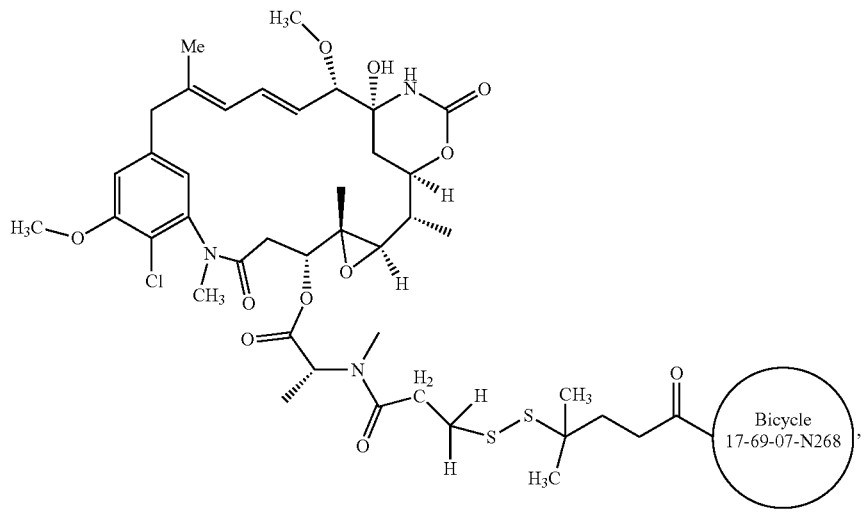 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]

or a pharmaceutically acceptable salt thereof.

8. The drug conjugate according to claim 1, which is BT17BDC-28:

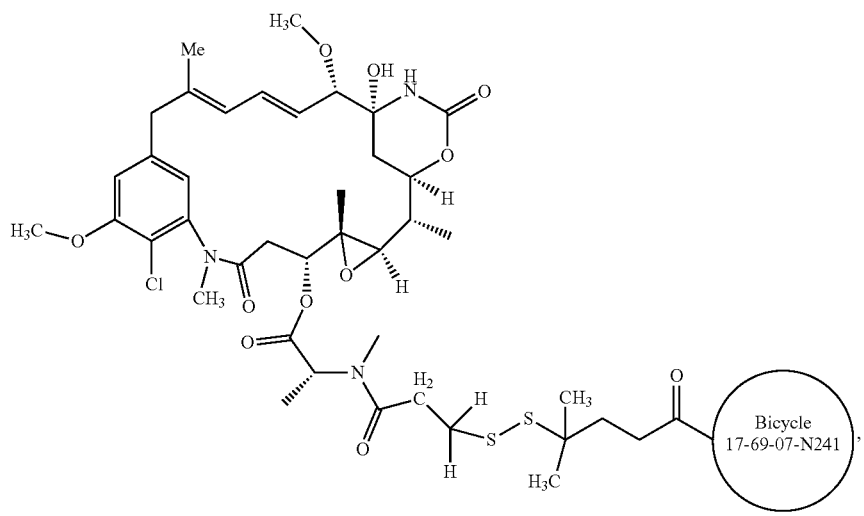 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]

or a pharmaceutically acceptable salt thereof.

9. The drug conjugate according to claim 1, which is a free acid, or a pharmaceutically acceptable salt selected from sodium, potassium, calcium, and ammonium salt.

10. The process according to claim 2, wherein the drug conjugate is BT17BDC-27:

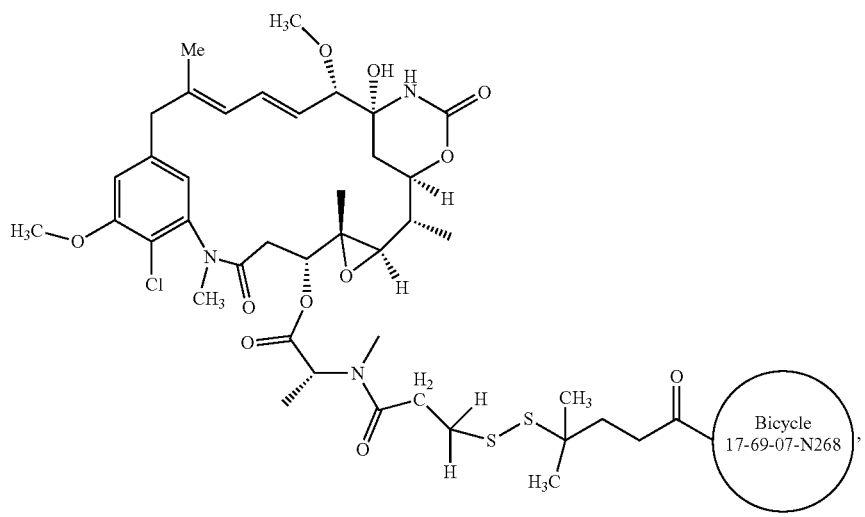 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
11. The process according to claim 2, wherein the drug conjugate is BT17BDC-28:
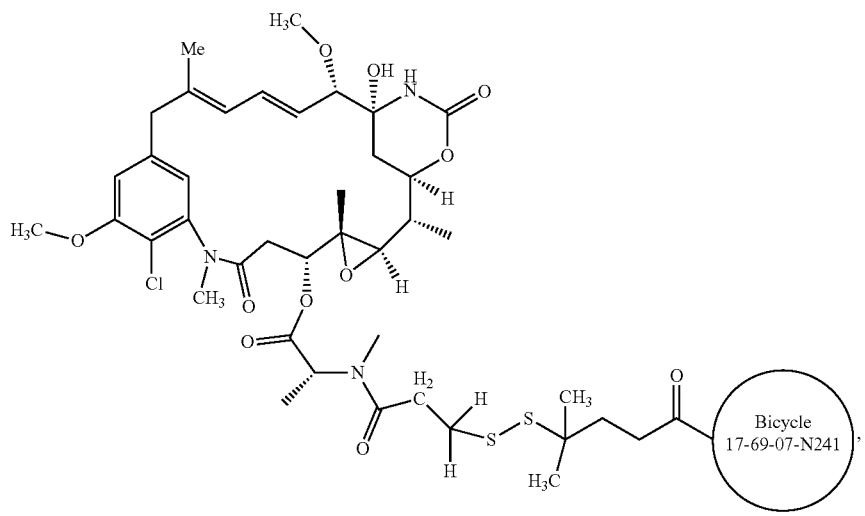 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
12. The pharmaceutical composition according to claim 3, wherein the drug conjugate is BT17BDC-27:

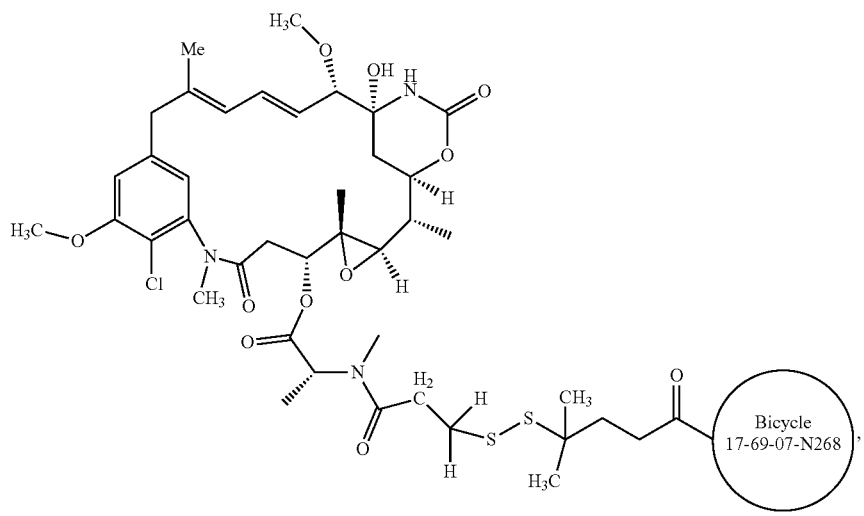 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
13. The pharmaceutical composition according to claim 3, wherein the drug conjugate is BT17BDC-28:
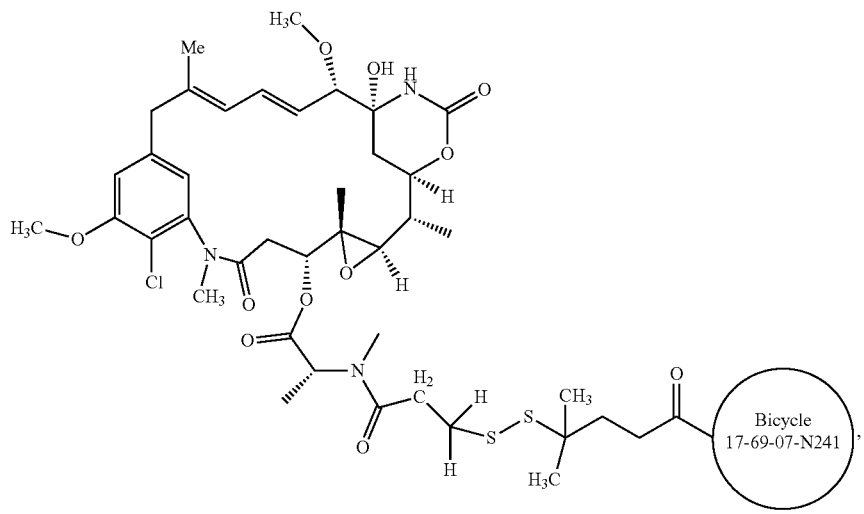 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
14. The method according to claim 4, wherein the drug conjugate is BT17BDC-27:

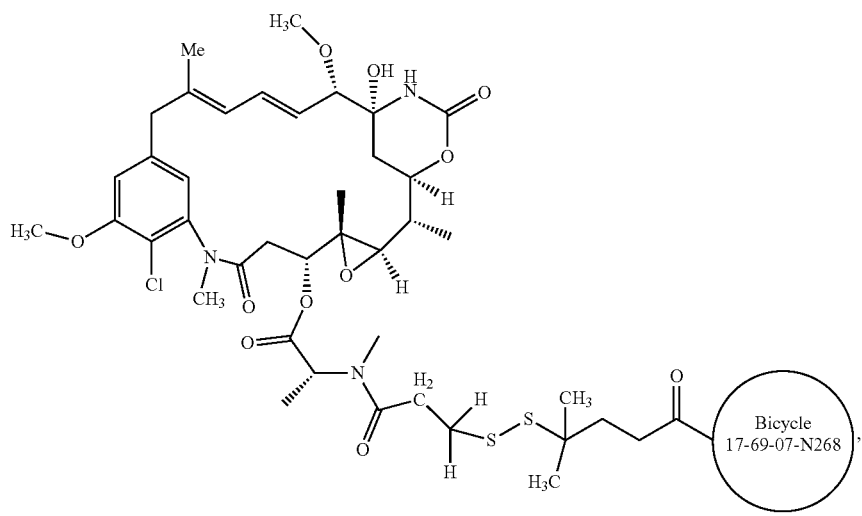 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
15. The method according to claim 4, wherein the drug conjugate is BT17BDC-28:
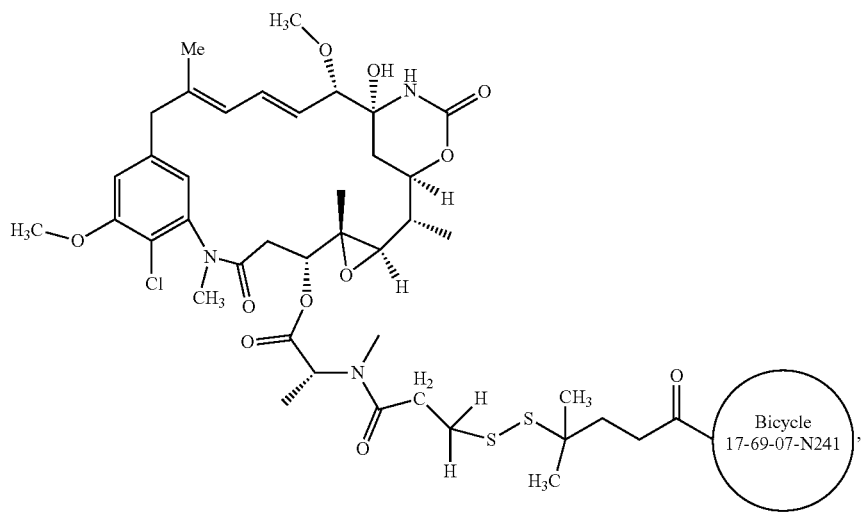 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
16. The method according to claim 6, wherein the drug conjugate is BT17BDC-27:

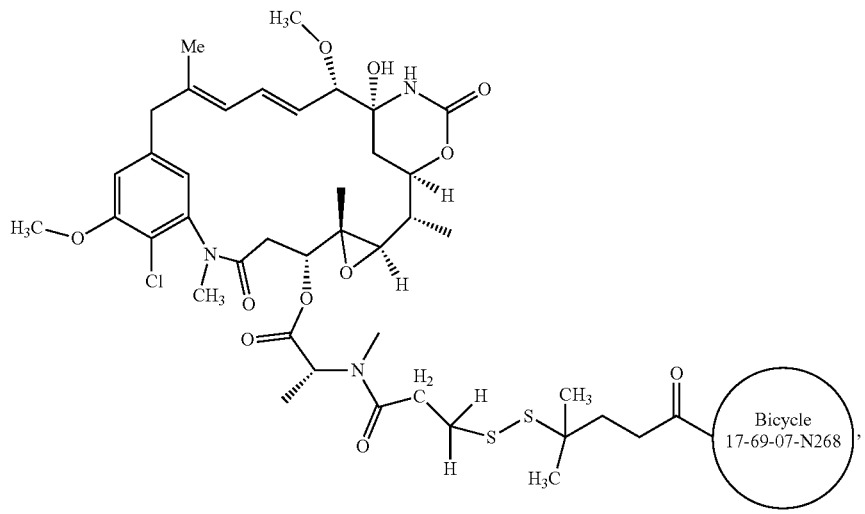 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
17. The method according to claim 6, wherein the drug conjugate is BT17BDC-28:
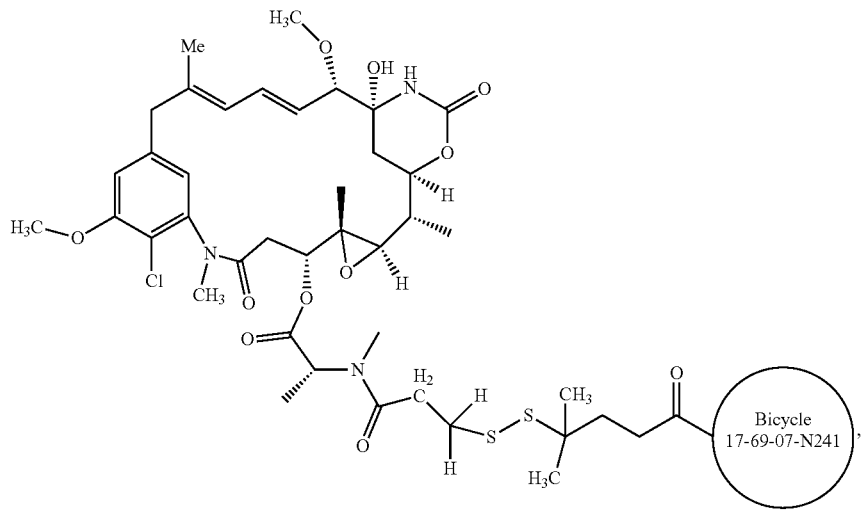 [SMILES: COc1cc2cc(c1Cl)N(C)C(=O)C[C@@H](OC(=O)[C@@H](C)N(C)C(=O)CCSSC(C)(C)CCC(C)=O)[C@@]1(C)O[C@@H]1[C@@H](C)[C@H]1C[C@](O)(NC(=O)O1)[C@@H](OC)/C=C/C=C(\C)C2]
or a pharmaceutically acceptable salt thereof.
* * * * *